US005593660A

United States Patent [19]
Krause et al.

[11] Patent Number: 5,593,660
[45] Date of Patent: Jan. 14, 1997

[54] CASCADE POLYMERS WITH IODOAROMATIC COMPOUNDS

[75] Inventors: Werner Krause; Franz-Karl Maier; Michael Bauer; Gabriele Schuhmann-Giampieri; Wolf-Rüdiger Press, all of Berlin, Germany

[73] Assignee: Schering Aktiengesellschaft, Berlin, Germany

[21] Appl. No.: 360,934

[22] Filed: Dec. 21, 1994

[30] Foreign Application Priority Data

Dec. 22, 1993 [DE] Germany .................. 43 44 464.4

[51] Int. Cl.⁶ .................................................. A61K 49/04
[52] U.S. Cl. .................. 424/9.451; 424/9.1; 424/9.3; 424/9.453; 430/80
[58] Field of Search ................. 424/9.1, 9.3, 9.451, 424/9.453; 430/80

[56] References Cited

U.S. PATENT DOCUMENTS 5,364,614  11/1994  Platzek et al. ........................ 424/9
5,399,620   3/1995  Wiessner et al. ..................... 525/71

*Primary Examiner*—Shelley A. Dodson
*Attorney, Agent, or Firm*—Millen, White, Zelano & Branigan, P.C.

[57] ABSTRACT

Iodine-containing dendrimeric polymers of general formula I $$A\text{—}(X)_b \qquad (I),$$

in which
A stands for a nitrogen-containing nucleus of basic multiplicity b, and
b stands for the numbers 1 to 8 and
X stands for a radical composed of $$\sum_{k=0}^{n-1} 2^k$$

reproduction units S and at most $2^n$ imaging radicals Z, in which
n determines the number of generations and stands for the numbers 1 to 10,
S and Z have various meanings, are valuable X-ray diagnostic agents.

27 Claims, 2 Drawing Sheets

CASCADE POLYMERS WITH IODOAROMATIC COMPOUNDS

SUMMARY OF THE INVENTION

The invention relates to new iodine-containing dendrimeric polymers, agents containing these compounds, the use of these polymeric compounds as contrast media as well as processes for the production of these compounds and pharmaceutical compositions containing same.

X-ray contrast media are indispensable auxiliary agents in the diagnosis of numerous diseases, such as, e.g., of atherosclerotic vascular processes, tumors, infarctions, diseases of the kidneys and efferent urinary passages and perfusion disorders, e.g., in the heart (ischemia, as well as inflammations).

The requirements, which are to be set for such contrast media, relate above all to a) a sufficiently high iodine concentration
of the solution used. As long as the agent is not diluted, the iodine concentration of a contrast medium is the sole parameter upon which X-ray opacity depends. This is especially the case in angiography, if the contrast medium is injected at a high speed by catheter in blood vessels and thus displaces the blood.

In a series of other studies, highly-concentrated contrast media are also desired, e.g., if the dilution in the body becomes otherwise too great (injection in the heart ventricles, the aorta or in the case of the intravenous digital subtraction angiography) or in unfavorable imaging conditions (for example, the path of rays through the body of a heavy patient can be very long);

b) the chemotoxicity,
an inherent property of the contrast medium solutions, which, among others, is associated with the lipophilia of the molecules, their protein-affinity and electron density. It manifests itself in clinical use by the occurrence of side effects, such as nausea, vomiting, of certain reactions of the circulatory system, urticaria, bronchospasm and other symptoms up to shock and death. Chemotoxic effects can be measured pharmacologically, e.g., as $LD_{50}$ after intravenous injection;

c) the viscosity,
a value, which is important for the process of the administration of the contrast media, e.g., if sizeable volumes (30–100 ml) of highly-concentrated and thus more highly viscous solutions are to be injected quickly. In addition to the poor injectability, more highly viscous contrast media also have the drawback of poor miscibility with blood (formation of streaks instead of homogenous filling of the cavity of the heart or blood vessels) and of the obstruction of the passage through capillaries, e.g., of the lung;

d) the osmolality
of the contrast medium solutions. In the case of the administration of solutions strongly hypertonic relative to the blood and tissue (the physiological value is 310 m osm/kg), water is driven from the cells, by which, i.a., cell membranes are destroyed and the entire electrolyte metabolism is disturbed. As a result, a large number of side effects, some of them serious, such as, e.g., drop in blood pressure, bradycardia up to cardiac arrest, disturbances of the blood-brain barrier, angialgias, etc., are caused;

e) a solubility,
which must be sufficiently high for the practical use of the contrast media with physiological pHs in water, but without compatibility and iodine content of the molecule being thus too greatly adversely affected at the same time;

f) a chemical stability
of the contrast medium solutions, which allows a heat sterilization, and produces a storability of at least 24 months.

For the visualization of vessels, X-ray contrast media would be desirable that are spread exclusively in the vascular space, i.e., the volume of distribution of the contrast medium should be analogous to the intravascular space. The contrast media previously used for the angiography are encumbered with the drawback that they very quickly leave the vascular space, since they are too small and hydrophilic, and can spread in the extracellular space. Moreover, their elimination takes place so quickly that generally a local administration by catheter (e.g., in the cranial area)—causing many difficulties for the patient—must be performed. Accordingly, blood pool agents (perfusion agents) would be desirable, which make it possible, after systemic administration with X-ray technology, to differentiate tissue well supplied with blood from tissue poorly supplied with blood to diagnose an ischemia. It would also be possible to differentiate infarcted tissue because of its anemia from surrounding healthy or ischemic tissue, when a vascular contrast medium is used. This is of special importance if, e.g., the point is to distinguish a cardiac infarction from an ischemia.

Another possibility of use consists in the diagnosis of vascular areas with reduced or increased permeability, which can be caused, e.g., by inflammations or tumors, as well as in lymphography and in mammography.

Therefore, there exists a demand for X-ray contrast media, which can mark the vascular space (blood pool agents). These compounds are to be distinguished by a good compatibility as well as by a high effectiveness (high increase of signal intensity or reduction of dose) and by the molecules remaining in the vascular space (no extravasation) as well as by a longer half-life in comparison to the contrast media used for the angiography.

The attempt to solve at least a part of these problems by using iodated macromolecular contrast media was previously successful only to a very limited extent.

Thus, the dextran derivatives described in International Patent Application WO 88/06162 exhibit a broad molecular weight distribution and, connected therewith, an incomplete elimination as well as an insufficient compatibility.

The iodine-containing polyamines disclosed in International Patent Application WO 93/10824 are not very well water-soluble and, moreover, relatively poorly compatible.

An object of the invention, therefore, is to make available new X-ray contrast media above all to detect and localize vascular diseases, which do not have the above-mentioned drawbacks.

Upon further study of the specification and appended claims, further objects and advantages of this invention will become apparent to those skilled in the art.

It has been found that iodine-containing dendrimeric polymers, which exhibit imaging radicals containing a nitrogen-containing nucleus and triiodoaromatic compounds and carrying aliphatic carboxy, sulfo or phosphono groups, are surprisingly excellently suited for the production of X-ray diagnostic agents, without exhibiting the above-mentioned drawbacks. The iodine-containing dendrimeric polymer according to the invention can be described by general formula I $$A\!-\!(X)_b \quad (I),$$

in which

A stands for a nitrogen-containing nucleus of basic multiplicity b, and b stands for the numbers 1 to 8 and X stands for a radical composed of $$\sum_{k=0}^{n-1} 2^k$$

reproduction units S having at most $2^n$ imaging radicals Z, in which n determines the number of generations and stands for the numbers 1 to 10, S stands for a radical of formula II

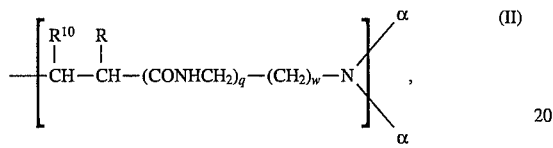

in which

R and $R^{10}$, independently of one another, stand for a hydrogen atom or a methyl group, w stands for the numbers 1 or 2, q stands for the numbers 0 or 1 and positions α for each generation up to n-1 is, in each case, occupied by a further reproduction unit S, and for n-th generation is, in each case, occupied by a radical Z or by radical $-(CO)_q-U-COOH$, in which q has the above-indicated meaning and U stands for a direct bond or an alkylene chain with up to 6 C atoms, which is optionally interrupted by 1–2 oxygen atoms and/or optionally substituted by 1–4 hydroxy groups and/or 1–2 carboxy groups, provided that at most 20% of positions α in the n-th generation are occupied by $-(CO)_q-U-COOH$, Z stands for an imaging radical Y—B containing at least an aliphatic carboxy, a sulfo or phosphono group and consisting of a linking element Y and a triiodoaromatic group B, and Y stands for a group —CO—, —CONH—, —CSNH—,

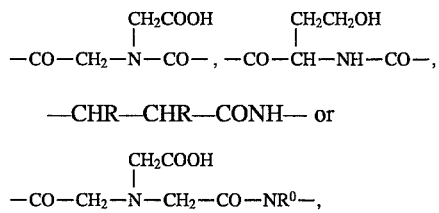

—CHR—CHR—CONH— or $$-CO-CH_2-\underset{\underset{CH_2COOH}{|}}{N}-CH_2-CO-NR^0-,$$

with R in the above-mentioned meaning and $R^0$ in the meaning of a hydrogen atom, a methyl or a carboxymethyl group and B stands for a benzene ring

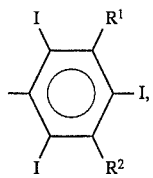

in which $R^1$ and $R^2$, each independently of one another, mean a hydrogen atom, a $-CONR^3R^4$ or $-NR^6COR^5$ group, and $R^3$ and $R^4$, independently of one another, stand for a hydrogen atom, a straight- or branched-chain or cyclic alkyl group with up to 12 C atoms optionally substituted by 1–5 hydroxy and/or 1–3 $C_1$–$C_3$ alkoxy and/or 1–3 carboxy, sulfo or phosphono group(s), $R^3$ and $R^4$ together with the nitrogen atom stand for a 5- or 6-membered ring optionally containing an oxygen atom, an $SO_2$ group or an $N-CO-R^7$ radical—with $R^7$ meaning a carboxy group or an alkyl group with up to 12 C atoms optionally containing 1–5 hydroxy, 1–3 $C_1$–$C_3$ alkoxy or 1–3 carboxy, sulfo or phosphono group(s), $R^5$ stands for a carboxy group, an alkyl group with up to 12 C atoms optionally interrupted by an oxygen atom and/or optionally substituted by 1–3 carboxy, sulfo or phosphono and/or 1–5 hydroxy and/or 1–3 $C_1$–$C_3$ alkoxy group(s), $R^6$ stands for a hydrogen atom, an alkyl group with up to 12 C atoms optionally substituted by 1–3 carboxy, sulfo or phosphono group(s) and/or optionally substituted by 1–3 hydroxy group(s) and/or 1–3 $C_1$–$C_3$ alkoxy groups, and reproduction units S must be identical only within a generation, as well as their salts with physiologically harmless organic and/or inorganic bases, amino acids or amino acid amides.

The aliphatic carboxy, sulfo or phosphono groups in imaging radical Z are groups which are not bonded directly to the benzene ring B. Thus, aliphatic carboxy, sulfo or phosphono groups can be, for example, contained in groups $R^3$, $R^4$, $R^5$ or $R^6$.

By dendrimers, dendritic polymeric molecules are to be understood, as they are described, e.g., in Angew. Chem. [Applied Chemistry] Vol. 104, 1609 (1992).

Preferably, n stands for the numbers 2 to 6.

As cascade nucleus A, there are suitable:

the nitrogen atom, radicals β-$NR^8$-β, β-$NR^8R^9$, the radicals of general formulas III, IV, V or VI,

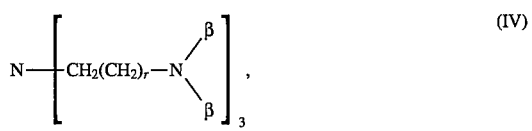

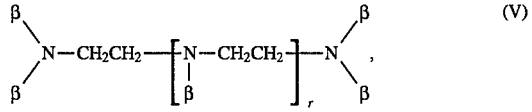

-continued

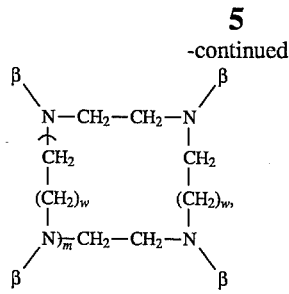

in which
R⁸ and R⁹, independently of one another, stand for a straight-chain or branched alkyl, aryl or aralkyl radical with up to 20 C atoms, which optionally is substituted by 1–4 hydroxy group(s),
β marks the binding site in radical X, in which the number of β's is to be treated as equivalent to basic multiplicity b,
V stands for a straight-chain or branched alkylene, arylene or aralkylene radical with up to 20 C atoms, which optionally is interrupted by 1–4 oxygen atom(s) and/or substituted by 1–4 hydroxy group(s),
r stands for the numbers 1, 2 or 3,
w stands for the numbers 1 or 2 and
m stands for the numbers 0, 1, 2 or 3.

The polymers according to the invention exhibit a molecular weight of 5,000 to 5,000,000, preferably 10,000 to 500,000, especially preferably from 20,000 to 100,000.

Basic multiplicity b is the sum of the free valences of the nitrogen-containing nucleus and stands for the numbers 1 to 8, preferably 1 to 6.

The nitrogen atom represents the simplest case of a cascade nucleus, whose three bonds (basic multiplicity b=3) are occupied in a first "inside layer" (generation 1) by three reproduction units S, which each carries a terminal $NH_2$ group (or the three hydrogen atoms of the underlying cascade starter ammonia have been substituted by three units S). The second layer (generation 2), introduced in a next reaction sequence, of reproduction unit S (which occupies A=nitrogen atom 3 times $2^1$=six bonds in the above-mentioned example) need not be identical with reproduction units S of the first generation. Preferably, reproduction units S are identical in all generations of a polymer. After at most 10, preferably 2 to 6, especially preferably 2 to 4 generations, the outermost layer exhibits b times $2^n$ (in the case of the nitrogen atom as cascade nucleus: 3 times $2^n$) positions α on the terminal nitrogen atoms of the last generation, which are occupied to 80–100% by imaging radicals Z and to at most 20% by radicals —$(CO)_q$—U—COOH.

As further preferred cascade starters $A(H)_b$, there can be listed, for example:
Tris-(2-aminoethyl)amine (b=6);
tris-(3-aminopropyl)amine (b=6);
diethylenetriamine (b=5);
triethylenetetraamine (b=6);
tetraethylenepentaamine (b=7);
tetramethylenediamine (b=4);
1,4,7-triazacyclononane (b=3);
1,4,7,10-tetraazacyclododecane (b=4);
1,4,7,10,13-pentaazacyclopentadecane (b=5);
1,4,8,11-tetraazacyclotetradecane (b=4);
2-hydroxy-1,3-propanediamine (b=4);
xylylenediamine (b=4);
hydroxyethylamine (b=2);
2,3-dihydroxypropylamine (b=2);
methylamine (b=2);
benzylamine (b=2);
aniline (b=2);
bis-(2,3-dihydroxylpropyl)amine (b=1);
2,3-dihydroxypropylmethylamine (b=1);
dibenzylamine (b=1);
1,8-diamino-3,6-dioxaoctane (b=4);
1,5-diamino-3-oxapentane (b=4).

X stands for a branch of the dendrimeric polymer, which is produced from the sum of reproduction units S and related imaging radicals Z.

Thus, e.g., a polymer composed of n=3 generations contains altogether
b times

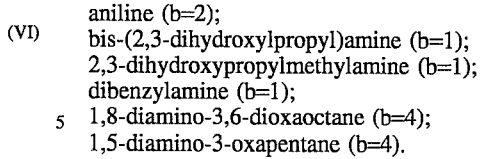

$(=2^0+2^1+2^2)$=b times 7 reproduction units S, and exhibits b times $2^3$=b times 8 terminal positions α, which are occupied by at most b times 8 imaging radicals Z.

Preferred reproduction units S are

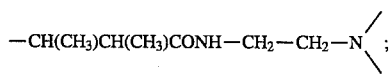

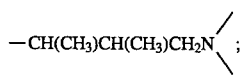

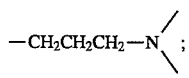

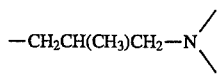

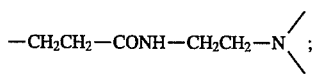

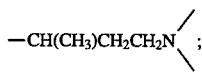

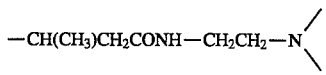

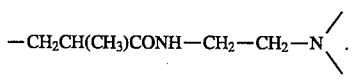

As alkyl groups R³, R⁴ and R⁷ contained in the R¹ and/or R² substituent of triiodoaromatic compound B, straight- or branched-chain or cyclic hydrocarbons with up to 12, preferably up to 10, especially preferably up to 6 C atoms are suitable, which is optionally substituted by 1–5, preferably 1–3 hydroxy and/or 1–3 $C_1$–$C_3$ alkoxy and/or 1–3, preferably one, carboxy, sulfo or phosphono group(s).

In particular, there can be mentioned, for example, the methyl, hydroxymethyl, ethyl, 2-hydroxyethyl, 2-hydroxy-1-(hydroxymethyl)-ethyl, 1-(hydroxymethyl)-ethyl, propyl, isopropyl, 2-hydroxypropyl, 3-hydroxypropyl, 2,3-dihydroxypropyl, 1,2,3-trihydroxypropyl, butyl, isobutyl, 2-hydroxybutyl, 3-hydroxybutyl, 4-hydroxybutyl, 2-, 3- and 4-hydroxy-2-methylbutyl, 2- and 3-hydroxyisobutyl, 2,3,4-trihydroxybutyl, 1,2,4-trihydroxybutyl, pentyl, cyclopentyl, cyclohexyl, 2,3,4,5,6-pentahydroxyhexyl, 2-methoxyethyl, carboxymethyl, 2-sulfoethyl, phosphonomethyl, 2-carboxyethyl, 10-hydroxydecyl, carboxy, 3-sulfopropyl, 2-phosphonoethyl group.

The heterocyclic 5- or 6-ring formed by $R^3$ and $R^4$ with the inclusion of the amide-nitrogen can optionally contain an oxygen atom, an $SO_2$ group or an N—CO—$R^7$ radical.

As suitable heterocycles, there can be mentioned, for example:

The piperidyl, pyrazolidyl, morpholinyl, N-substituted piperazinyl, S,S-dioxothiomorpholinyl ring.

As radicals $R^5$ and $R^6$ contained in the $R^1$ and/or $R^2$ substituent of triiodoaromatic compound B, the following can be mentioned as examples in addition to the corresponding radicals listed for $R^3$, $R^4$, $R^7$:

Carboxymethoxymethyl, 5-carboxy-1,5-dihydroxy-3-oxapentyl, 2-carboxy-1-hydroxy-ethyl, 3-carboxy-2-oxapropyl group.

The alkyl, aryl or aralkyl radical or alkylene, arylene or aralkylene radical standing for $R^8$ and $R^9$ or V can be straight-chain or branched and contain up to 20, preferably up to 12 C atoms. The $R^8$ and $R^9$ substituents can each be substituted by 1–4, preferably 1–2 hydroxy group(s), the chain standing for V (optionally in addition) can be interrupted by 1–4, preferably 1–2 oxygen atoms. As examples, the following groups can be mentioned:

Ethylene, butylene, 1-methylpropylene, propylene, 3,6-dioxaoctylene, xylylene, 2-hydroxy-propylene, 3-oxapentylene.

The alkylene chain standing for U can exhibit up to 6, preferably up to 2 C atoms, and optionally can be interrupted by 1–2 oxygen atoms and/or optionally substituted by 1–4, preferably 1–2 hydroxy groups, and/or 1–2 carboxy groups. As examples for radicals —$(CO)_q$—U—COOH, there can be listed:

—CO(CH$_2$)$_2$COOH; —COCOOH;
—CO(CHOH)$_2$COOH; —COCH$_2$OCH$_2$COOH;
—COCH$_2$COOH; —COCH(OCH$_3$)COOH,
—CH$_2$CH$_2$COOH, —CH(CH$_3$)CH$_2$COOH,
—CH$_2$CH(CH$_3$)COOH, —CH(CH$_3$)CH(CH$_3$)COOH,
in which radicals —CO(CH$_2$)$_2$COOH, —COCH$_2$OCH$_2$COOH, —CH$_2$CH$_2$COOH are preferred.

The acidic hydrogen atoms of the acid groups contained in the polymers can be replaced completely or partially by cations of inorganic and/or organic bases, amino acids or amino acid amides.

Suitable cations of inorganic bases are, for example, the lithium, the potassium, the calcium, the magnesium and especially the sodium ion. Suitable cations of organic bases are, among others, those of primary, secondary or tertiary amines, such as, e.g., ethanolamine, diethanolamine, morpholine, glucamine, N,N-dimethylglucamine and especially N-methylglucamine. Suitable cations of amino acids are, for example, those of lysine, arginine and ornithine as well as the amides of otherwise acidic or neutral amino acids.

The compounds according to the invention exhibit the initially depicted desired properties. They contain the number of triiodoaromatic compounds required for their use as X-ray contrast media. They are spread only in the vascular space and can therefore mark the latter with diagnostic radiology.

The iodine content of the compounds according to the invention on the average is about 40 wt. %. Thus, in comparison to other macromolecules containing iodoaromatic compounds, such as the dextran derivatives described in WO 88/06162 (about 2 to 35%), the iodine content of the compounds according to the invention is in some cases higher by a multiple. The compounds according to the invention can be surprisingly mixed in any ratio with water in contrast to the dextran derivatives described in WO 88/06162, which results in a higher contrast medium concentration in the blood vessels shortly after injection and thus has an advantageous effect on the differentiation of the blood vessels. The value of osmolality responsible for side effects, such as pains, damages to the blood vessels and cardiovascular disorders is clearly reduced and is no longer hyperosmolar as is otherwise often observed in the case of X-ray contrast media (example 1j: 220 [mosmol/kg] at 37° C., 130 mg of iodine/ml). The osmolality of the compounds according to the invention is also clearly less than that of the dextran compounds (440 mosmol/kg at 90 mg of iodine/ml) described in WO 88/06162.

The chemotoxicity, responsible for the acute compatibility, of the compounds according to the invention (example 6c; i.v.-$LD_{50}$ mouse>5 g of iodine/kg) is clearly improved both in comparison to the macromolecular contrast media based on carbohydrates (WO 88/06162) and to the examples based on polyamines described in WO 93/10824.

In comparison to the macromolecules based on dextran, the viscosity of the compounds according to the invention is also clearly lower, which allows a bolus injection and thus clearly better differentiation of the blood vessels relative to the surrounding tissue (example 6c: 4.02 mPas at 37° C. and 100 mg of iodine/ml; example 10 of WO 88/06162: 26 mPas at 37° C. and 90 mg of iodine/ml).

With the compounds according to the invention, it has been possible to produce macromolecules with defined molecular weight. Such macromolecular contrast media exactly defined in their molecular size with iodoaromatic compounds were not previously accessible.

The macromolecules based on dextran, e.g., dextran 40,000 (Rheomacrodex®) are a mixture of macromolecules of various sizes, whose average molecular weight lies, e.g., at 40,000 daltons. But in this mixture, dextran molecules are also present which are larger than 50,000 or 60,000 daltons. This portion of high-molecular dextran compounds may lie between 5 and 10% of the total amount. As known from the literature (G. Arturson and G. Wallenius, The Renal Clearance of Dextran of Different Molecular Sizes in Normal Humans, Scandinav. J. Clin. & Lab. Investigation 1:81–86, 1964), dextran molecules of this size are no longer glomerularly filtered, and the renal clearance of these molecules is therefore almost zero. Also, the compounds described in patents EP 0206551, EP 0436316 and in examples 1, 2 and 3 of WO 93/10824, cannot be completely eliminated because of their high-molecular portions after i.v. administration. But from a diagnostic agent, it is expected that after intravenous injection, it is completely eliminated from the body within a short period. The remaining compounds described in WO 93/10824, on the other hand, leave the intravascular space too quickly and are thus not suitable as perfusion agents. With the compounds according to the invention, it has been surprisingly possible for the first time to make available iodine-containing polymers which only slowly leave the vascular space, but simultaneously also pass the capillaries of the kidneys and thus are completely eliminated. Because of the molecular structure, the compounds according to the invention in the first 15 minutes after intravenous administration show a blood concentration, which is about four times higher than in the extracellular X-ray contrast media, such as, e.g., Ultravist® (see figure in Example 20). In this case, the cascade polymers are present in the body only in the vascular space, i.e., the distribution volume is about 0.05 l/kg. After intravenous administration of 300 mg of iodine/kg in the rat, the compounds according to the invention showed a complete elimination (retention<1% of the dose, 14 days after intravenous administration). Thus, it is possible for the first time to produce macromolecular contrast media with triiodoaromatic compounds appropriate for the body.

The cascade polymers according to the invention are used as contrast media for the visualization of the vessels by diagnostic radiology. It is thus possible to distinguish ischemic tissue from normal tissue. But also other damages to the blood-tissue barrier can be detected with these compounds. In the case of inflammations and tumors in the brain, the blood-brain barrier is damaged so that the contrast medium can infiltrate the diseased tissue and thus the diseased tissue can be detected with the diagnostic radiology. Because of the impermeability of the intact blood-brain barrier, inflammations and tumors could also be detected for small, but hydrophilic molecules even with the low-molecular Ultravist®. But if the cascade polymers according to the invention are used in these cases, the dose can be reduced to one fourth, since the macromolecules are spread in a space one fourth the size, namely only in the vascular space, i.e., to achieve identical concentrations in the blood, a fourth of the dose is sufficient.

At the same time, perfusion measurements can be performed with the compounds according to the invention, e.g., on the myocardium, which was possible only to a limited extent with the low-molecular compounds such as Ultravist®, since these molecules quickly "go out" into the interstitial space. In the case of the low-molecular compounds, the "going out" into the interstice often resulted in poor definition of the image, which can be avoided by the compounds according to the invention. At the same time, the measuring time relative to the low-molecular compounds can be greatly lengthened.

Another advantage of this invention lies in the fact that now macromolecules with differently lipophilic or hydrophilic triiodaryl radicals have become accessible. As a result, the possibility is provided to control compatibility and pharmacokinetics of these cascade polymers by variously substituted triiodaryl radicals.

The production of the iodine-containing dendrimeric polymers according to the invention takes place in that dendrimeric polymers of general formula I'

$$A—(X')_b \qquad (I'),$$

in which

A and b have the meanings indicated in formula I and

X' has the meaning indicated for X in formula I, but unlike X for the n-th generation, positions α are not occupied by radicals Z and optionally —(CO)$_q$—U—COOH, but by hydrogen atoms, are reacted with compounds of general formula II $$Y'—B' \qquad (II),$$

in which

Y' stands for a radical to be converted to Y containing a carbonyl, thiocarbonyl, activated carbonyl or a CHR=CR group—with R meaning a hydrogen atom or a methyl group—and B' has the meaning of a triiodoaromatic compound indicated for B, and carboxy and hydroxy groups contained in B are, however, present in protected form, and then positions α optionally not occupied by radicals Z are acylated or alkylated with a reagent introducing radical —(CO)$_q$—U—COOH.

As examples for an activated carbonyl group in radicals Y' of the feedstocks of general formula II, anhydride, p-nitrophenylester, lactone and acid chloride can be mentioned. As examples for Y', there can be mentioned the radicals COCl; NCO; NCS;

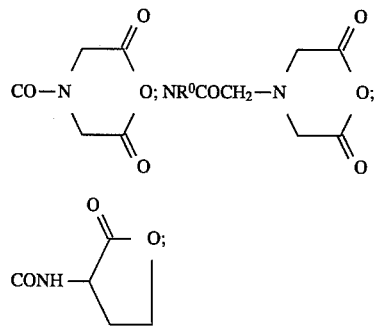

and NHCO—CR=CHR.

As acid protective groups, lower alkyl, aryl and aralkyl groups, for example, the methyl, ethyl, propyl, nbutyl, t-butyl, phenyl, benzyl, diphenylmethyl, triphenyl methyl, bis(p-nitrophenyl)-methyl group, as well as trialkylsilyl groups, are suitable.

The cleavage of the protective groups takes place according to the processes known to one skilled in the art [see, e.g., E. Wünsch, Methoden der Org. Chemie [Methods of Organic Chemistry] (Houben Weyl), Vol. XV/1, 4th edition 1974, p. 315 ff], for example by hydrolysis, hydrogenolysis, alkaline saponification of esters with alkali in aqueous-alcoholic solution at temperatures of 0° to 50° C., acid saponification with mineral acids or in the case of, e.g., tert-butyl esters with the help of trifluoroacetic acid.

As hydroxy protective groups, e.g., the benzyl, 4-methoxybenzyl, 4-nitrobenzyl, trityl, diphenylmethyl, trimethylsilyl, dimethyl-t-butylsilyl, diphenyl-t-butylsilyl groups are suitable.

The hydroxy groups can also be present, e.g., as THP-ether, α-alkoxyethylether, MEM-ether or as esters with aromatic or aliphatic carboxylic acids, such as e.g., acetic acid or benzoic acid. In the case of polyols, the hydroxy groups can also be protected in the form of ketals with, e.g., acetone, acetaldehyde, cyclohexanone or benzaldehyde.

In the case of simultaneous presence of carboxyl groups, hydroxy groups can also be present protected by intramolecular esterification to the corresponding lactones.

The hydroxy protective groups can be released according to the methods in the literature known to one skilled in the art, e.g., by hydrogenolysis, reductive cleavage with lithium/ammonia, acid treatment of ethers and ketals or alkali treatment of the esters (see, e.g., "Protective Groups in Organic Synthesis," T. W. Greene, John Wiley and Sons 1981).

The various processes for the production of polymers according to the invention as well as the initial compounds required for them are known in principle to one skilled in the art. They are based on the reaction of the terminal amino groups of the respectively desired generation of dendrimeric polymers of general formula I' with the compounds of general formula II suitable for generating linking elements Y bound on triiodoaromatic compounds B.

Thus, the reaction of N,N-bis(carboxymethyl)-amine- or amide-substituted triiodoaromatic compounds, present in anhydride form, takes place in liquid reaction media, such as, for example, water, dipolar aprotic solvents, such as diethyl ether, tetrahydrofuran, dioxane, acetonitrile, N-methylpyrrolidone, dimethylformamide, dimethylacetamide and the like or their mixtures by adding amines, such as, e.g., triethylamine, N-ethyldiisopropylamine, N,N-di-methyl-4-aminopyridine. The reaction temperatures lie between about −80° C. and 160° C., and temperatures from 20° C. to 80° C. are preferred. The reaction times lie between 0.5 hour and 7 days, preferably between 1 hour and 48 hours.

The production of the acid anhydrides can take place according to known processes, e.g., according to the process with acetic anhydride in pyridine described in U.S. Pat. No. 3,660,388 or in DE 16 95 050. But in certain cases, it is advantageous to perform the water cleavage gently with carbodiimides in a suitable solvent, such as, e.g., dimethylformamide or dimethylacetamide.

The reactions of the isocyanate- or isothiocyanate-substituted triiodoaromatic compounds take place according to methods known in the literature (DOS 26 10 500, EP 0 431 838), for example in aprotic solvents, such as, for example, DMSO, DMF, DMA or else in water or hydrous solvent mixtures at temperatures of 0°–120° C., preferably 20°–75° C. The reaction times generally lie between 1–48 hours, preferably 3–24 hours.

The reaction of triiodoaromatic compounds containing lactone structures with corresponding dendrimeric polyamines is possible, e.g., analogous to the process for aminolysis of 2-acylamino-4-butyrolactones described by T. Sheradsky, Y. Knobler and M. Frankel in J. Org. Chem., 26, 2710 (1961).

Addition reactions of a triiodoaromatic compound exhibiting olefinic substituent CHR=CR—CONH are performed, e.g., according to the specification indicated in Org. Synth. Coll. Vol. VI, p. 75 (1988), by a triiodated acrylamide being reacted in polar solvents, such as DMF, DMA, pyridine, ethanol with the desired polyamine.

The acylations of the terminal amino groups of the polymers of general formula I' with triiodoaromatic compounds, which contain an acid chloride substituent, are performed according to the processes known to one skilled in the art, e.g., analogously to the specification in EP 0015867. The reaction is generally performed in polar aprotic solvents, such as, e.g., DMF, DMA, or in mixtures of polar aprotic solvents with water, in the presence of an acid trap, such as, e.g., tertiary amine (e.g., triethylamine, trimethylamine, N,N-dimethylaminopyridine, 1,5-diazabicyclo[4.3.0]nonene-5 (DBN), 1,5-diazabicyclo[5.4.0]undecene-5 (DBU), alkali-, alkaline-earth carbonate, hydrogencarbonate or hydroxide (e.g., potassium carbonate, sodium carbonate, lithium hydroxide, potassium hydroxide) at temperatures between 0°–120° C., preferably 20°–80° C. and reaction times of 1–36 hours.

The subsequent acylation or alkylation of the terminal amino groups optionally not bound to imaging radicals Y—B takes place analogously to specifications known in the literature, see, e.g., Org. Syn. Coll. Vol. 4, 5 (1963).

The neutralization of the acid groups can be performed with the help of inorganic bases (e.g., hydroxides, carbonates or bicarbonates) of, for example, sodium, potassium, lithium, magnesium or calcium and/or organic bases, such as, among others, primary, secondary and tertiary amines, such as, for example, ethanolamine, morpholine, glucamine, N-methyl- and N,N-dimethylglucamine, as well as basic amino acids, such as, for example, lysine, arginine and ornithine or of amides of originally neutral or acidic amino acids.

The dendrimeric polymers of formula I' used as feedstocks are produced analogously to methods known in the literature (e.g., European Patent Application EP 0 430 863; U.S. Pat. No. 4,507,466; International Application WO 93/14147).

The iodated aromatic compounds used in the various processes are known or can be easily generated from those known.

Thus, e.g., in German laid-open specifications DE 29 28 417 and DE 29 09 439, iodated aromatic compounds are described, which are easily reacted with, e.g., thionyl chloride to the corresponding acid chloride group-containing aromatic compounds.

Isocyanate- or isothiocyanate-substituted triiodoaromatic compounds can be produced by reaction of the corresponding aniline derivatives with phosgene or thiophosgene in aprotic solvents, such as, e.g., 1,2-dichloroethane, dichloromethane, pyridine, dimethyl sulfoxide, tetrahydrofuran, dioxane, diethyl ether, ethyl acetate, (literature: DOS 25 41 491).

Triiodoaromatic compounds contained in a lactone radical are attained, for example, by reaction of a triiodobenzoylchloride derivative with 2-amino-4-butyrolactone hydrochloride. A reaction of this type is described, e.g., by J. Brennan and P. J. Murphy in Tetrahedron Lett., 29 (17), 2063 (1988).

Triiodoaromatic compounds with an olefinic substituent CHR=CR—CONH can be obtained analogously to the indications in WO 85/01727.

Other aromatic radicals can be produced as described in M. Sovak; Radiocontrast Agents, Handbook of Experimental Pharmacology Vol. 73 (1984), Springer-Verlag, Berlin—Heidelberg—New York—Tokyo or in European Patent EP 0 015 867.

A further object of the invention are pharmaceutical agents, which contain at least one of the compounds according to the invention.

The invention further relates to a process for the production of these agents, which is characterized in that the radio-opaque substance is brought into a form suitable for enteral or parenteral administration with the additives and stabilizers usual in galenicals. The pharmaceutical preparation can generally be matched at will to the specific needs of the user. The concentration of the new X-ray contrast media in the aqueous medium depends entirely on the method of diagnostic radiology. The iodine content of the solutions is usually about 50–450 mg/ml, preferably 70–200 mg/ml.

The resulting agents are then optionally heat-sterilized. They are administered as a function of the iodine content and the method of diagnostic radiology used or formulation of the problem generally in a dose of about 30 mg of iodine/kg −2000 mg of iodine/kg.

The administration of the aqueous solution of X-ray contrast medium can take place enterally or parenterally, thus orally, rectally, intravenously, intraarterially, intravascularly, intracutaneously, subcutaneously (lymphography), subarachnoidally (myelography).

Suitable additives are, for example, physiologically harmless buffers (such as, e.g., tromethamine, bicarbonate, phosphate, citrate), stabilizers (such as, e.g., DTPA, sodium edetate, calcium-disodium edetate), or—if necessary—electrolytes (such as, e.g., sodium chloride) or—if necessary—antioxidants (such as, e.g., ascorbic acid) or else substances to match the osmolality (such as, e.g., mannitol, glucose).

If suspensions or solutions of the agents, according to the invention, in water or physiological salt solution are desired for enteral administration or other purposes, they are mixed with one or more auxiliary agents usual in galenicals (e.g., methyl cellulose, lactose, mannitol) and/or surfactants (e.g., lecithin, Tween®, Myrj® and/or aromatic substances for taste correction (e.g., essential oils).

The following examples are used for more detailed explanation of the objects of the invention, without intending to be limited to these objects.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 43 44 464.4, are hereby incorporated by reference.

EXAMPLES

Example 1

Production of the 3-(3-Carboxypropionylamino)-5-(2,3-dihydroxypropyl carbamoyl)-2,4,6-triiodobenzoyl derivative of the 48-fold primary cascade amine [see Example 1h]

a) Tris-[N,N-bis-(methoxycarbonylethyl)-2-aminoethyl]-amine 14.69 g (0.100 mol) of tris-(2-aminoethyl)-amine, dissolved in 20 ml of methanol, is instilled in 103.3 g (1.20 mol) of methyl acrylate with stirring at 20° C. The batch is stirred under argon atmosphere for 5 days at room temperature and for 2 days at 50° C. Then, it is concentrated by evaporation in a vacuum and excess methyl acrylate is removed by azeotropic distillation with toluene. The residue is taken up in 150 ml of methanol and 30 ml of diethyl ether, absorptively precipitated with 150 ml of hexane and, after separation of the hexane phase, concentrated by evaporation in a vacuum. The product is obtained as yellowish liquid, which is further reacted without purification.

Yield: 66.8 g (100% of theory)

Analysis (relative to the solventless substance): Cld: C 54.37 H 8.21 N 8.45 O 28.97 Fnd: C 54.51 H 8.13 N 8.26 b) Production of a 6-fold primary cascade amine

A solution of 67.5 g (0.102 mol) of the hexamethyl ester, produced under example 1a), in 135 ml of methanol is instilled in 1363 ml (20.25 mol) of ethylenediamine, stirred under argon at room temperature, within 2 hours. After 5 days of stirring at room temperature, the batch is concentrated by evaporation in a vacuum. The residue is taken up in methanol and washed 5 times with diethyl ether. The methanolic solution is concentrated by evaporation in a vacuum and the residue is dried on a high vacuum.

Yield: 72.6 g (85.6% of theory) of yellowish oil

Analysis (relative to the solventless substance): Cld: C 52.03 H 9.46 N 26.96 O 11.55 Fnd: C 51.90 H 9.62 N 27.17 c) Production of a 12-fold dendrimeric methyl ester

A solution of 43.73 g (0.053 mol) of the hexamine, produced under example 1b), in 120 ml of methanol is instilled in 559.5 g (6.28 mol) of methyl acrylate with stirring at 20° C. After 5 days of stirring at room temperature, the batch is concentrated by evaporation and excess methyl acrylate is removed to the greatest possible extent by azeotropic distillation with toluene under reduced pressure.

The residue is taken up in a little methanol and washed several times with diethyl ether/hexane. The crude product that is concentrated by evaporation is purified by chromatography on silica gel 60 (Merck) (eluent: methylene chloride/methanol). After concentration by evaporation of the product fractions, a colorless oil is obtained.

Yield: 95.6 g (96.8% of theory)

Analysis (relative to the solventless substance): Cld: C 54.12 H 8.11 N 12.02 O 25.75 Fnd: C 53.93 H 8.35 N 11.84 d) Production of a 12-fold primary cascade amine

A solution of 40.2 g (21.5 mmol) of the dodecamethyl ester, produced under example 1c), in 250 ml of methanol is instilled in 2.0 l (30 mol) of ethylenediamine, stirred under argon at room temperature, within 4 hours. The batch is stirred for 5 days at room temperature, then concentrated by evaporation, taken up in a little methanol and washed several times with diethyl ether. The methanolic product solution is concentrated by evaporation in a vacuum, and the yellowish, oily residue is dried on a high vacuum.

Yield: 47.3 g (100% of theory)

Analysis (relative to the solventless substance): Cld: C 52.39 H 9.07 N 25.46 O 13.09 Fnd: C 52.18 H 9.25 N 25.63 e) Production of a 24-fold dendrimeric methyl ester

A solution of 40.9 g (18.6 mmol) of the dodecaamine, produced under example 1d), in 180 ml of methanol is instilled in 570 ml (6.30 mol) of methyl acrylate with stirring at room temperature. The batch is stirred for 6 days at room temperature, then concentrated by evaporation in a vacuum, and excess methyl acrylate is removed to the greatest possible extent by azeotropic distillation with toluene under reduced pressure. The residue is taken up in a little methanol and washed several times with diethyl ether. The methanolic solution is concentrated by evaporation and the residue is purified on silica gel 60 (Merck) (eluent: methanol/pyridine). After concentration by evaporation of the product fractions, a colorless oil is obtained.

Yield: 73.4 g (92.5% of theory)

Analysis (relative to the solventless substance): Cld: C 54.05 H 8.08 N 13.13 O 24.75 Fnd: C 54.27 H 7.82 N 13.02 f) Production of a 24-fold primary cascade amine

A solution of 72.7 g.(17.0 mmol) of the cascade compound, produced under example 1e), in 300 ml of methanol is instilled in 3.0 l (45 mol) of ethylenediamine, stirred under argon at room temperature, within 4 hours. The batch is stirred for 5 days at room temperature, then concentrated by evaporation, taken up in a little methanol and washed several times with diethyl ether. The methanolic product solution is concentrated by evaporation in a vacuum and the yellowish, oily residue is dried on a high vacuum.

Yield: 82.6 g (98% of theory)

Analysis (relative to the solventless substance): Cld: C 52.51 H 8.94 N 24.95 O 13.60 Fnd: C 52.44 H 9.12 N 25.21 g) Production of a 48-fold dendrimeric methyl ester

A solution of 58.5 g (11.8 mmol) of the cascade amine, produced under example 1f), in 200 ml of methanol is instilled in 590.9 g (6.77 mol) of methyl acrylate with stirring at room temperature. The batch is stirred for 7 days at room temperature, then concentrated by evaporation in a vacuum, and excess methyl acrylate is removed to the greatest possible extent by azeotropic distillation with toluene under reduced pressure. The residue is taken up in a little methanol and washed several times with diethyl ether. The methanolic solution is concentrated by evaporation and the residue is purified on silica gel 60 (Merck) (eluent: methanol/pyridine). After concentration by evaporation of the product fractions, a yellowish oil is obtained.

Yield: 87.04 g (81.3% of theory)

Analysis (relative to the solventless substance): Cld: C 54.01 H 8.07 N 13.59 O 24.34 Fnd: C 54.30 H 7.86 N 13.33 h) Production of a 48-fold primary cascade amine

A solution of 78.4 g (8.64 mmol) of the cascade compound, produced under example 1g), in 300 ml of methanol is instilled in 3.0 l (45 mol) of ethylenediamine, stirred under argon at room temperature, within 4 hours. The batch is stirred for 6 days at room temperature, then concentrated by evaporation, taken up in a little methanol and washed several times with diethyl ether. The methanolic product solution is concentrated by evaporation in a vacuum, and the yellowish oily residue is dried on a high vacuum.

Yield: 82.4 g (91.2% of theory)

Analysis (relative to the solventless substance): Cld: C 52.57 H 8.88 N 24.74 O 13.82 Fnd: C 52.74 H 8.93 N 24.74 i) 5-(3-Ethoxycarbonylpropionylamino)-2,4,6-triiodoisophthalic acid-N-(2,3-diacetoxypropyl)-amide-chloride 24.7 g (150 mmol) of succinic acid chloride-monoethyl ester at room temperature is added to a suspension of 73.4 g (100 mmol) of 5-amino-2,4,6-triiodoisophthalic acid-N-(2,3-diacetoxypropyl)-amide-chloride (EP 0308364) in 500 ml of anhydrous dioxane stirred with exclusion of moisture. The batch is refluxed for several hours until, according to thin-layer chromatography, feedstock is no longer detectable; then, it is concentrated by evaporation, the residue is taken up in dichloromethane and shaken out with saturated aqueous sodium bicarbonate solution. After drying on anhydrous magnesium sulfate, the organic phase is concentrated by evaporation, and the residue is recrystallized from ethyl acetate/tert-butyl methyl ether.

Yield: 74.8 g (86.7% of theory) of colorless crystals

Analysis (relative to the solventless substance): Cld: C 29.84 H 2.57 Cl 4.11 I 44.14 N 3.25 O 16.69 Fnd: C 30.19 H 2.63 Cl 4.21 I 44.07 N 3.18 j) Production of the 3-(3-carboxypropionylamino)-5-(2,3-dihydroxypropyl carbamoyl)-2,4,6-triiodobenzoyl derivative of the 48-fold primary cascade amine [see example 1b)]

An emulsion, consisting of 6.6 g (0.63 mmol) of the cascade amine, produced under example 1h), 9.54 ml (68.8 mmol) of triethylamine and 50 ml of water, is slowly instilled in a solution of 39.6 g (45.9 mmol) of the acid chloride, produced under example 1i), in 200 ml of N,N-dimethylformamide, mechanically stirred at room temperature. The batch is stirred for 2 days at room temperature, then mixed with 100 ml of 2N sodium hydroxide solution and stirred for 2 hours at 50° and then, after cooling to room temperature, it is neutralized with 2N hydrochloric acid and then subjected to an ultrafiltration, in which low-molecular components are separated by a hollow fiber membrane (H1 P3-20, Amicon). The aqueous product solution is filtered with a cellulose-membrane filter (pore size 0.45 μm, Sartorius) and freeze-dried.

Yield: 24.7 g (87.3% of theory) of colorless lyophilizate

Analysis (relative to the anhydrous substance): Cld: C 31.61 H 3.48 I 40.89 N 8.78 O 15.25 Fnd: C 31.89 H 3.62 I 40.60 N 8.95

Example 2

Production of the 3-carboxymethylcarbamoyl-5-sodium carboxylatomethylcarbamoyl-2,4,6-triiodophenylcarbamoyl derivative of the 48-fold primary cascade amine [see example 1h)]

a) 5-Amino-2,4,6-triiodoisophthalic acid-N,N'-bis-(methoxycarbonylmethyl)-diamide (EP 0129932)

A solution of 59.6 g (100 mmol) of 5-amino-2,4,6-triiodoisophthalic acid dichloride in 300 ml of N,N-dimethylformamide is mixed with 27.6 g (220 mmol) of glycine methyl ester hydrochloride and 61.0 ml (440 mmol) of triethylamine. A suspension results, which is stirred overnight at room temperature under argon. After concentration by evaporation of the suspension on a vacuum, the residue is recrystallized from methanol.

Yield: 66.3 g (94.6% of theory)

Analysis (relative to the solventless substance): Cld: C 23.99 H 2.01 I 54.31 N 5.99 O 13.69 Fnd: C 23.95 H 2.14 I 54.28 N 6.09 b) 5-Isocyanato-2,4,6-triiodoisophthalic acid-N,N'-bis-(methoxycarbonylmethyl)-diamide 147 ml (73.8 mmol) of a 2N toluenic phosgene solution and 2 ml of N,N-dimethylformamide are added to a suspension of 20.7 g (29.5 mmol) of the aniline derivative, produced under example 2a), in 200 ml of 1,2-dichloroethane, stirred at 60° C. oil bath temperature under argon atmosphere. After completion of the reaction of the aniline derivative, the batch is concentrated by evaporation on a vacuum, the residue is absorptively precipitated with anhydrous ethyl acetate, suctioned off under nitrogen atmosphere and dried on an oil pump vacuum.

Yield: 21.5 g (100% of theory) of light beige solid

Analysis (relative to the solventless substance): Cld: C 24.78 H 1.66 I 52.37 N 5.78 O 15.40 Fnd: C 24.82 H 1.73 I 52.35 N 5.70 c) Production of the 3-carboxymethylcarbamoyl-5-sodium carboxylatomethylcarbamoyl-2,4,6-triiodophenylcarbamoyl derivative of the 48-fold primary cascade amine [see example 1h)]

A solution of 3.72 g (0.36 mmol) of the cascade amine, produced under example 1h), in 37 ml of anhydrous dimethyl sulfoxide is slowly instilled in a solution of 18.7 g(22.7 mmol) of the isocyanate, produced under example 2b), in 200 ml of anhydrous dimethyl sulfoxide stirred at room temperature under argon atmosphere. The batch is stirred for 2 days at room temperature, then mixed with 30 ml of 2N sodium hydroxide solution and stirred for 2 hours at 50° C. After cooling to room temperature, the solution is neutralized with 2N hydrochloric acid and then subjected to an ultrafiltration, in which low-molecular components are separated by a hollow fiber membrane (H1 P3-20, Amicon). The aqueous product solution is filtered with a cellulose-membrane filter (pore size 0.45 μm, Sartorius) and freeze-dried.

Yield: 13.23 g (81.6% of theory) of yellowish lyophilizate

Analysis (relative to the anhydrous substance): Cld: C 28.81 H 2.81 I 40.59 N 10.20 Na 2.45 O 15.14 Fnd: C 29.10 H 2.98 I 40.28 N 10.41 Na 2.77

Example 3

Production of the 3,5-bis-[(N-carboxymethyl)-sodium carboxylatomethylcarbamoyl]-2,4,6-triiodophenylcarbamoyl derivative of the 48-fold primary cascade amine [see example 1h)]

a) 5-Amino-2,4,6-triiodoisophthalic acid-N,N,N',N'-tetrakis-(methoxycarbonylmethyl)-diamide A solution of 47.2 g (79.2 mmol) of 5-amino-2,4,6-triiodoisophthalic acid dichloride in 250 ml of N,N-dimethylformamide is mixed with 34.4 g (174 mmol) of iminodiacetic acid dimethyl ester hydrochloride (Synthesis according to Dubsky, Graenacher, Chem. Ber. 50, 1693 (1917)) and 48.2 ml (348 mmol) of triethylamine. A suspension results, which is stirred overnight at room temperature under argon. After concentration by evaporation of the suspension on a vacuum, the residue is taken up in dichloromethane and shaken out with aqueous sodium bicarbonate solution. The organic phase is dried with anhydrous magnesium sulfate, filtered and, after concentration by evaporation on silica gel 60 (Merck, Darmstadt), chromatographed (mobile solvent: dichloromethane/methanol). The product fractions are evaporated to dryness in a vacuum.

Yield: 57.1 g (85.3% of theory) of colorless solid

Analysis (relative to the solventless substance): Cld: C 28.42 H 2.62 I 45.05 N 4.97 O 18.93 Fnd: C 28.61 H 2.77 I 44.83 N 4.72 b) 5-Isocyanato-2,4,6-triiodoisophthalic acid-N,N,N',N'-tetrakis-(methoxycarbonylmethyl)-diamide 45.3 ml (90.5 mmol) of a 2N toluenic phosgene solution and 3 ml of N,N-dimethylformamide are added to a solution of 30.6 g (36.2 mmol) of the aniline, produced under example 3a), in 300 ml of 1,2-dichloroethane stirred at 60° C. oil bath temperature under argon atmosphere. After completion of the reaction of the aniline derivative, the batch is concentrated by evaporation on a vacuum, the residue is absorptively precipitated with tert-butyl methyl ether, suctioned off under nitrogen atmosphere and dried on an oil pump vacuum.

Yield: 30.3 g (96.2% of theory) of reddish solid

Analysis (relative to the solventless substance): Cld: C 28.95 H 2.31 I 43.70 N 4.82 O 20.20 Fnd: C 29.14 H 2.46 I 43.56 N 4.73 c) Production of the 3,5-bis-[(N-carboxymethyl)-sodium carboxylatomethylcarbamoyl]-2,4,6-triiodophenylcarbamoyl derivative of the 48-fold primary cascade amine [see example 1h)]

A solution of 4.79 g (0.46 mmol) of the cascade amine, produced under example 1h), in 48 ml of anhydrous dimethyl sulfoxide is slowly instilled in a solution of 28,8 g (33.1 mmol) of the isocyanate, produced under example 3b), in 250 ml of anhydrous dimethyl sulfoxide, stirred at room temperature under argon atmosphere. The batch is stirred for 2 days at room temperature, then mixed with 66 ml of 2N sodium hydroxide solution and stirred for 2 hours at 50° C. After cooling to room temperature, the solution is neutralized with 2N hydrochloric acid and then subjected to an ultrafiltration, in which the low-molecular components are separated by a hollow fiber membrane (H1 P3-20, Amicon). The aqueous product solution is filtered with a cellulose-membrane filter (pore size 0.45 μm, Sartorius) and freeze-dried.

Yield: 20.6 g (86.7% of theory) of yellowish lyophilizate

Analysis (relative to the anhydrous substance): Cld: C 29.58 H 2.73 I 35.38 N 8.90 Na 4.27 O 19.14 Fnd: C 29.84 H 2.90 I 35.11 N 9.21 Na 3.92

Example 4

Production of the 3-[(N-carboxymethyl)-methylcarbamoyl]-5-[(N-sodium carboxylatomethyl)-methylcarbamoyl]-2,4,6-triiodophenylcarbamoyl derivative of the 48-fold primary cascade amine [see example 1h)]

a) 5-Amino-2,4,6-triiodoisophthalic acid-N,N'-bis-(ethoxycarbonylmethyl)-N,N'-dimethyl-diamide A solution of 59.6 g (100 mmol) of 5-amino-2,4,6-triiodoisophthalic acid dichloride in 300 ml of N,N-dimethylformamide is mixed with 33.8 g (220 mmol) of sarcosine ethyl ester hydrochloride and 61.0 ml (440 mmol) of triethylamine. A suspension results, which is stirred overnight at room temperature under argon. After the concentration by evaporation of the suspension on a vacuum, the residue is taken up in dichloromethane and shaken out with aqueous sodium bicarbonate solution. The organic phase is dried with anhydrous magnesium sulfate, filtered and concentrated by evaporation. The residue is recrystallized from isopropanol.

Yield: 59.8 g (79% of theory) of colorless solid

Analysis (relative to the solventless substance): Cld: C 28.56 H 2.93 I 50.29 N 5.55 O 12.68 Fnd: C 28.73 H 3.09 I 50.02 N 5.77 b) 5-Isocyanato-2,4,6-triiodoisophthalic acid-N,N'-bis-(ethoxycarbonylmethyl)-N,N'-dimethyl-diamide 31.7 ml (63.4 mmol) of a 2N toluenic phosgene solution and 2 ml of N,N-dimethylformamide are added to a solution of 19.2 g (25.4 mmol) of the aniline derivative, produced under example 4a), in 200 ml of 1,2-dichloroethane stirred at 60° C. oil bath temperature under argon atmosphere. After completion of the reaction of the aniline derivative, the batch is concentrated by evaporation on a vacuum, the residue is absorptively precipitated with tert-butyl methyl ether, suctioned off under nitrogen atmosphere and dried on an oil pump vacuum.

Yield: 19.26 g (97% of theory) of reddish solid

Analysis (relative to the solventless substance): Cld: C 29.14 H 2.57 I 48.62 N 5.37 O 14.30 Fnd: C 29.08 H 2.63 I 48.50 N 5.23 c) Production of the 3-[(N-carboxymethyl)-methylcarbamoyl]-5-[(N-sodium carboxylatomethyl)-methylcarbamoyl]-2,4,6-triiodophenylcarbamoyl derivative of the 48-fold primary cascade amine [see example 1h)]

A solution of 3.27 g (0.31 mmol) of the cascade amine, produced under example 1h), in 33 ml of anhydrous dimethyl sulfoxide is slowly instilled in a solution of 17.7 g (22.6 mmol) of the isocyanate, produced under example 4b), in 150 ml of anhydrous dimethyl sulfoxide stirred at room temperature under argon atmosphere. The batch is stirred for 2 days at room temperature, then mixed with 100 ml of 2N sodium hydroxide solution and stirred for 2 hours at 50° C. After cooling to room temperature, the solution is neutralized with 2N hydrochloric acid and then subjected to an ultrafiltration, in which low-molecular components are separated by a hollow fiber membrane (H1 P3-20, Amicon). The aqueous product solution is filtered with a cellulose-membrane filter (pore size 0.45 μm, Sartorius) and freeze-dried.

Yield: 13.1 g (91.3% of theory) of colorless lyophilizate

Analysis (relative to the anhydrous substance): Cld: C 30.46 H 3.14 I 39.41 N 9.91 Na 2.38 O 14.70 Fnd: C 30.61 H 3.27 I 39.18 N 10.16 Na 2.15

Example 5

Production of the 3-carboxyformylamino-5-(2,3-dihydroxypropylcarbamoyl)-2,4,6-triiodobenzoyl derivative of the 48-fold primary cascade amine [see example 1h)]

a) 5-(Ethoxycarbonylformylamino)-2,4,6-triiodoisophthalic acid-N-(2,3-diacetoxypropyl)-amide-chloride 20.5 g (150 mmol) of oxalic acid chloride-monoethyl ester is added to a suspension of 73.4 g (100 mmol) of 5-amino-2,4,6-triiodoisophthalic acid-N-(2,3-diacetoxypropyl)-amide-chloride (EP 0308364) in 300 ml of anhydrous dioxane stirred with exclusion of moisture at room temperature. The batch is refluxed for several hours until, according to thin-layer chromatography, feedstock is no longer detectable, then, it is concentrated by evaporation, the residue is taken up in dichloromethane and shaken out with saturated aqueous sodium bicarbonate solution. After drying on anhydrous magnesium sulfate, the organic phase is concentrated by evaporation, and the residue is recrystallized from ethyl acetate/tert-butyl methyl ether.

Yield: 73.9 g (88.6% of theory) of colorless crystals

Analysis (relative to the solventless substance): Cld: C 27.35 H 2.17 Cl 4.25 I 45.62 N 3.36 O 17.25 Fnd: C 27.33 H 2.28 Cl 4.17 I 45.49 N 3.42 b) Production of the 3-carboxyformylamino-5-(2,3-dihydroxypropylcarbamoyl)-2,4,6-triiodobenzoyl derivative of the 48-fold primary cascade amine [see example 1h]

An emulsion consisting of 10.9 g (1.04 mmol) of the cascade amine produced under example 1h), 15.6 ml (0.112 mol) of triethylamine and 80 ml of water is slowly instilled in a solution of 62.6 g (75.0 mmol) of the acid chloride, produced under example 5a), in 350 ml of N,N-dimethylformamide mechanically stirred at room temperature. The batch is stirred for 2 days at room temperature, then mixed with 150 ml of 2N sodium hydroxide solution and stirred for 2 hours at 50° C. After cooling to room temperature, the solution is neutralized with 2N hydrochloric acid and then subjected to an ultrafiltration, in which low-molecular components are separated by a hollow fiber membrane (H1 P3-20, Amicon). The aqueous product solution is filtered with a cellulose-membrane filter (pore size 0.45 µm, Sartorius) and freeze-dried.

Yield: 41.9 g (93.0% of theory) of colorless lyophilizate

Analysis (relative to the anhydrous substance): Cld: C 29.93 H 3.14 I 42.16 N 9.05 O 15.73 Fnd: C 30.12 H 3.42 I 41.83 N 9.27

Example 6

Production of the 3-(4-carboxy-3-oxabutyrylamino)-5-(2,3-dihydroxypropylcarbamoyl)-2,4,6-triiodobenzoyl derivative of the 48-fold primary cascade amine [see example 1h]

a) Diglycolic acid chloride-monoisopropyl ester 46.4 g (400 mmol) of diglycolic anhydride is added to 24.0 g (400 mmol) of anhydrous isopropanol with exclusion of moisture. The temperature of the exothermic reaction is moderated to 90°–100° C. with a water bath. After 1 hour, the reaction mixture is allowed to cool and it is mixed with 32.0 ml (440 mmol) of thionyl chloride and 0.1 ml of N,N-dimethylformamide and allowed to stir for 15 hours at room temperature and for 1 hour at 50° C. The title compound is obtained by distillation at 0.01 torr and a boiling temperature of 100°–101° C.

Yield: 67.6 g (86.8% of theory) of colorless liquid Gas chromatography (100% method): content 96.4%

Analysis (relative to the solventless substance): Cld: C 43.20 H 5.70 Cl 18.22 O 32.88 Fnd: C 43.34 H 5.83 Cl 18.01 b) 5-[4-(2-Methylethyloxycarbonyl)-3-oxabutyrylamino]-2,4,6-triiodoisophthalic acid-N-(2,3-diacetoxypropyl)-amide-chloride 29.2 g (150 mmol) of the acid chloride produced according to example 6a) is added to a suspension of 73.4 g (100 mmol) of 5-amino-2,4,6-triiodoisophthalic acid-N-(2,3-diacetoxypropyl)-amide-chloride (EP 0308364) in 500 ml of anhydrous dioxane, stirred with exclusion of moisture, at room temperature. The batch is refluxed for several hours until, according to thin-layer chromatography, feedstock is no longer detectable, then it is concentrated by evaporation, the residue is taken up in dichloromethane and shaken out with saturated, aqueous sodium bicarbonate solution. After drying on anhydrous magnesium sulfate, the organic phase is concentrated by evaporation, and the residue is recrystallized from ethyl acetate/tert-butyl methyl ether.

Yield: 68.2 g (76.4% of theory) of colorless crystals

Analysis (relative to the solventless substance): Cld: C 29.60 H 2.71 Cl 3.97 I 42.65 N 3.14 O 32.88 Fnd: C 29.77 H 2.83 Cl 3.92 I 42.41 N 3.38 c) Production of the 3-(4-carboxy-3-oxabutyrylamino)-5-(2,3-dihydroxypropylcarbamoyl)-2,4,6-triiodobenzoyl derivative of the 48-fold primary cascade amine [see example 1h]

An emulsion consisting of 7.2 g (0.69 mmol) of the cascade amine produced under example 1h), 10.4 ml (75.0 mmol) of triethylamine and 50 ml of water is slowly instilled in a solution of 44.6 g (50.0 mmol) of the acid chloride, produced under example 6b), in 200 ml of N,N-dimethylformamide mechanically stirred at room temperature. The batch is stirred for 2 days at room temperature, then mixed with 100 ml of 2n sodium hydroxide solution and stirred for 2 hours at 50° C. After cooling to room temperature, the solution is neutralized with 2n hydrochloric acid and then subjected to an ultrafiltration, in which low-molecular components are separated by a hollow fiber membrane (H1 P3-20, Amicon). The aqueous product solution is filtered with a cellulose-membrane filter (pore size 0.45 µm, Sartorius) and freeze-dried.

Yield: 31.49 g (83.7% of theory) of colorless lyophilizate

Analysis (relative to the anhydrous substance): Cld: C 31.07 H 3.42 I 40.20 N 8.63 O 16.68 Fnd: C 31.37 H 3.65 I 39.94 N 8.82

Example 7

Production of the 3-[(N-carboxymethyl)-sodium carboxylatomethylcarbamoyl]-5-methoxy-acetylamino-2,4,6-triiodobenzoyl derivative of the 48-fold primary cascade amine [see example 1h]

a) 5-Methoxyacetylamino-2,4,6-triiodoisophthalic acid-N,N-bis-(methoxycarbonylmethyl)-amide chloride A solution of 66.8 g (100 mmol) of 5-methoxyacetylamino-2,4,6-triiodoisophthalic acid dichloride (EP 0 015 867) in 300 ml of anhydrous N,N-dimethylformamide is mixed with 21.75 g (110 mmol) of iminodiacetic acid dimethyl ester hydrochloride (synthesis according to Dubsky, Graenacher, Chem. Ber. 50, 1693 (1917)) and 30.5 ml (220 mmol) of triethylamine. A suspension results, which is stirred for 14 hours at room temperature under argon. The batch is taken up in dichloromethane, shaken out once with water, twice with 2N aqueous citric acid and once with aqueous sodium bicarbonate solution. The organic phase is dried on anhydrous magnesium sulfate and concentrated by evaporation in a vacuum. By instilling tert-butyl ether in the concentrated solution, the title compound can precipitate as crystalline solid, which is suctioned off and dried in a vacuum.

Yield: 57.4 g (72.4% of theory)

Analysis (relative to the solventless substance): Cld: C 25.76 H 2.04 Cl 4.47 I 48.04 N 3.54 O 16.15 Fnd: C 25.82 H 2.11 Cl 4.48 I 48.01 N 3.38 b) Production of the 3-[(N-carboxymethyl)-sodium carboxylatomethylcarbamoyl]-5-methoxyacetylamino-2,4,6-triiodobenzoyl derivative of the 48-fold primary cascade amine [see example 1h]

An emulsion consisting of 6.6 g (0.64 mmol) of the cascade amine produced under example 1h), 9.30 ml (68.7 mmol) of triethylamine and 50 ml of water is slowly instilled in a solution of 36.3 g (45.8 mmol) of the acid chloride, produced under example 7a), in 200 ml of N,N-dimethylformamide mechanically stirred at room temperature. The batch is stirred for 2 days at room temperature, then mixed with 100 ml of 2N sodium hydroxide solution and stirred for 2 hours at 50° C. After cooling to room temperature, the solution is neutralized with 2N hydrochloric acid and then subjected to an ultrafiltration, in which low-molecular components are separated by a hollow fiber membrane (H1 P3-20, Amicon). The aqueous product solution is filtered with a cellulose-membrane filter (pore size 0.45 µm, Sartorius) and freeze-dried.

Yield: 26.9 g (90.5% of theory) of colorless lyophilizate

Analysis (relative to the anhydrous substance): Cld: C 30.43 H 3.04 I 39.37 N 8.45 Na 2.38 O 16.34 Fnd: C 30.75 H 3.27 I 39.04 N 8.58 Na 2.06

Example 8

Production of the N-[3,5-di-(acetylamino)-2,4,6-triiodobenzoyl]-N-(carboxymethyl)-glycyl derivative of the 48-fold primary cascade amine [see example 1h]

a) 3,5-Dinitrobenzoyl-N,N-bis-(carboxymethyl)-amide 133.1 g (1.00 mol) of iminodiacetic acid is dissolved in 1.50 l of 2N sodium hydroxide solution and mixed with 230.6 g (1.00 mol) of 3,5-dinitrobenzoyl chloride with mechanical stirring. A dark red solution results, from which the title compound is precipitated by acidification with semiconcentrated hydrochloric acid. The precipitate is suctioned off, washed with water and dried in a vacuum.

Yield: 260.5 g (79.6% of theory) of colorless crystals

Analysis (relative to the anhydrous substance): Cld: C 40.38 H 2.77 N 12.84 O 44.01 Fnd: C 40.42 H 2.85 N 12.63 b) 3,5-Diaminobenzoyl-N,N-bis-(carboxymethyl)-amide 32.7 g (100 mmol) of the dinitro compound described under example 8a) is introduced in 500 ml of methanol, mixed with 1.6 g of palladium catalyst (10% palladium on activated carbon) and hydrogenated by shaking with hydrogen. After absorption of the theoretic amount of hydrogen, it is filtered off from the catalyst and evaporated to dryness. The residue is further reacted without purification.

Yield: 26.7 g (100% of theory) of colorless solid.

Analysis (relative to the solventless substance): Cld: C 49.44 H 4.90 N 15.72 O 29.93 Fnd: C 49.40 H 4.98 N 15.68 c) 3,5-Diamino-2,4,6-triiodobenzoyl-N,N-bis-(carboxymethyl)-amide 24.7 g (92.4 mmol) of the compound produced under example 8b) is mixed in 200 ml of water and with 150 ml of a 2N iodomonochloride solution within 30 minutes. The mixture is stirred for 12 hours at room temperature and the precipitate formed is suctioned off. The solid is suspended in water, treated with 10 g of sodium hydrogen sulfite and again isolated. The material is dissolved in 300 ml of water by adding 30% sodium hydroxide solution at pH 8, mixed with 2 g of activated carbon, stirred for 5 hours and filtered. By acidification of the filtrate with concentrated hydrochloric acid, a precipitate is formed, which is suctioned off and dried in a vacuum.

Yield: 40.1 g (67.3% of theory) of colorless solid

Analysis (relative to the anhydrous substance): Cld: C 20.49 H 1.59 I 59.03 N 6.52 O 12.40 Fnd: C 20.61 H 1.63 I 58.86 N 6.68 d) 3,5-Bis-(acetylamino)-2,4,6-triiodobenzoyl-N,N-bis-(carboxymethyl)-amide 38.6 g (59.9 mmol) of the compound produced under example 8c) is introduced in a mixture of 180 ml of acetic anhydride and 0.5 ml of concentrated sulfuric acid. After stirring overnight at room temperature, diethyl ether is added, and the solid formed is filtered off. The solid is dissolved in 300 ml of water by adding 30% sodium hydroxide solution at pH 9, and then further precipitated by acidification with concentrated hydrochloric acid at pH 1. The precipitate is suctioned off and dried in a vacuum.

Yield: 29.9 g (68.6% of theory) of colorless solid

Analysis (relative to the anhydrous substance): Cld: C 24.71 H 1.94 I 52.22 N 5.76 O 15.36 Fnd: C 24.65 H 2.03 I 52.31 N 5.65 e) N-[3,5-Bis-(acetylamino)-2,4,6-triiodobenzoyl]-2,6-dioxomorpholine 28.1 g (38.5 mmol) of the compound produced under example 8d) is dissolved in 56 ml of anhydrous pyridine, mixed with 7.3 ml (77 mmol) of acetic anhydride and stirred for 10 hours at room temperature with exclusion of moisture. By instilling anhydrous diethyl ether, the anhydride formed is precipitated, filtered off and dried in a vacuum.

Yield: 27.4 g (100% of theory) of light beige solid

Analysis (relative to the solventless substance): Cld: C 25.34 H 1.70 I 53.55 N 5.91 O 13.50 Fnd: C 25.21 H 1.83 I 53.58 N 5.86 O 13.73 f) Production of the N-[3,5-di-(acetylamino)-2,4,6-triiodobenzoyl]-N-(carboxymethyl)-glycyl derivative of the 48-fold primary cascade amine [see example 1h]

An emulsion consisting of 5.2 g (0.50 mmol) of the cascade amine produced under example 1h), 7.5 ml (54.0 mmol) of triethylamine and 30 ml of water is slowly instilled in a solution of 25.6 g (36.0 mmol) of the anhydride, produced under example 8e), in 200 ml of N,N-dimethylformamide mechanically stirred at room temperature. The batch is stirred for 2 days at room temperature, then neutralized with 2N hydrochloric acid and subjected to an ultrafiltration, in which low-molecular components are separated by a hollow fiber membrane (H1 P3-20, Amicon). The aqueous product solution is filtered with a cellulose-membrane filter (pore size 0.45 μm, Sartorius) and freeze-dried.

Yield: 19.5 g (87.5% of theory)

Analysis (relative to the anhydrous substance): Cld: C 31.71 H 3.38 I 41.02 N 10.31 O 13.58 Fnd: C 31.98 H 3.52 I 40.76 N 10.54

Example 9

Production of the 3-[(N-carboxymethyl)-methoxyacetylamino]-5-(2,3-dihydroxy-propylcarbamoyl)-2,4,6-triiodobenzoyl derivative of the 48-fold primary cascade amine [see example 1h]

a) 5-Methoxyacetylamino-2,4,6-triiodoisophthalic acid-N-(2,3-diacetoxypropyl)-amide-chloride 24.7 g (150 mmol) of methoxyacetyl chloride is added to a suspension of 73.4 g (100 mmol) of 5-amino-2,4,6-triiodoisophthalic acid-N-(2,3-diacetoxypropyl)-amide-chloride (EP 0308364) in 500 ml of anhydrous dioxane, stirred with exclusion of moisture, at room temperature. The batch is refluxed for several hours, until, according to thin-layer chromatography, feedstock is no longer detectable, then it is concentrated by evaporation, the residue is taken up in dichloromethane and shaken out with saturated aqueous sodium bicarbonate solution. After drying on anhydrous magnesium sulfate, the organic phase is concentrated by evaporation, and the residue is recrystallized from ethyl acetate/tert-butyl methyl ether.

Yield: 73.2 g (90.7% of theory) of colorless crystals

Analysis (relative to the solventless substance): Cld: C 26.81 H 2.25 Cl 4.40 I 47.21 N 3.47 O 15.87 Fnd: C 26.79 H 2.32 Cl 4.48 I 47.13 N 3.44 b) 5-Methoxyacetylamino-2,4,6-triiodoisophthalic acid-N-(2,3-dihydroxypropyl)-monoamide 60.6 g (75.1 mmol) of the acid chloride produced under example 9a) is introduced in 376 ml of 1N sodium hydroxide solution and stirred vigorously for about 45 minutes under nitrogen atmosphere. The completeness of the conversion is checked by thin-layer chromatography and the product solution is used without working-up for the next stage.

c) N-Carboxymethyl-5-methoxyacetylamino-2,4,6-triiodoisophthalic acid-N'-(2,3-dihydroxypropyl)-monoamide The solution of the feedstock (75.1 mmol), produced according to example 9b), is mixed with 17.5 g (150.2 mmol) of the sodium salt of the chloroacetic acid under nitrogen atmosphere and stirred for about 18 hours at 90° C. The solution is adjusted with 2N hydrochloric acid to pH 1 and completely concentrated by evaporation. The residue is chromatographed on silica gel 60 (Merck) (mobile solvent dichloromethane/methanol/ acetic acid (2:2:1)). The product fractions are evaporated to dryness in a vacuum and the residue is recrystallized from methanol/isopropanol.

Yield: 47.7 g (83.3% of theory) of colorless crystals

Analysis (relative to the solventless substance): Cld: C 25.22 H 2.25 I 49.96 N 3.68 O 18.90 Fnd: C 25.31 H 2.51 I 49.82 N 3.72 d) N-Methoxycarbonylmethyl-5-methoxyacetylamino-2,4,6-triiodoisophthalic acid-N'-(2,3-dihydroxypropyl)-monoamide 45.8 g (60.1 mmol) of the compound produced under example 9c) is introduced in 150 ml of anhydrous methanol and stirred under nitrogen atmosphere. 5.6 ml (6.6 mmol) of dimethyl sulfite is instilled with stirring. The batch is stirred for 4 hours at room temperature and refluxed for 1 hour. Then, it is concentrated by evaporation, the residue is absorptively precipitated with isopropanol, filtered off and dried in a vacuum.

Yield: 41.2 g (88.4% of theory) of colorless crystals

Analysis (relative to the solventless substance): Cld: C 26.31 H 2.47 I 49.06 N 3.61 O 18.55 Fnd: C 26.21 H 2.35 I 49.13 N 3.53 e) N-Methoxycarbonylmethyl-5-methoxyacetylamino-2,4,6-triiodoisophthalic acid-N'-(2,3-diacetoxypropyl)-monoamide 38.2 g (49.2 mmol) of the compound produced under example 9d) is stirred in a mixture of 16.3 ml (172 mmol) of acetic anhydride and 150 ml of dioxane with exclusion of moisture. 0.60 g (4.9 mmol) of 4-N,N-dimethylaminopyridine is added and stirred for 2 hours at 50° C. Then, the batch is concentrated by evaporation, the residue is absorptively precipitated with ethyl acetate/tert-butyl methyl ether, filtered off and dried in a vacuum.

Yield: 37.0 g (87.4% of theory) of colorless solid

Analysis (relative to the solventless substance): Cld: C 29.32 H 2.70 I 44.26 N 3.26 O 20.46 Fnd: C 29.38 H 2.77 I 44.17 N 3.30 f) N-Methoxycarbonylmethyl-5-methoxyacetylamino-2,4,6-triiodoisophthalic acid-N'-(2,3-diacetoxypropyl)-amidechloride 35.6 g (41.4 mmol) of the compound described under example 9e) is introduced in 150 ml of 1,2-dichloroethane. 0.1 ml of N,N-dimethylformamide and 4.50 ml (62.1 mmol) of thionyl chloride are added to the suspension, stirred with exclusion of moisture at room temperature. The batch is refluxed until no more gas generation can be observed. The now existing solution is concentrated by evaporation on a vacuum, the residue is taken up in dichloromethane and shaken out with saturated, aqueous sodium bicarbonate solution. The organic phase is dried on anhydrous magnesium sulfate and filtered. By instilling tert-butyl methyl ether in the filtrate that is concentrated by evaporation, a colorless precipitate is obtained which is suctioned off and dried in a vacuum.

Yield: 30.6 g (84.1% of theory) of colorless solid

Analysis (relative to the solventless substance): Cld: C 28.71 H 2.52 Cl 4.04 I 43.33 N 3.19 O 18.21 Fnd: C 28.81 H 2.80 Cl 4.28 I 43.17 N 3.21 g) Production of the 3-[(N-carboxymethyl)-methoxyacetylamino]-5-(2,3-dihydroxypropylcarbamoyl)-2,4,6-triiodobenzoyl derivative of the 48-fold primary cascade amine [see example 1h)]

An emulsion consisting of 3.49 g (0.34 mmol) of the cascade amine produced under example 1h), 5.0 ml (36.2 mmol) of triethylamine and 30 ml of water is slowly instilled in a solution of 21.2 g (24.1 mmol) of the acid chloride, produced under example 9f), in 100 ml of N,N-dimethylformamide mechanically stirred at room temperature. The batch is stirred for 2 days at room temperature, then mixed with 60 ml of 2N sodium hydroxide solution and stirred for 2 hours at 50° C. After cooling to room temperature, the solution is neutralized with 2N hydrochloric acid and subjected to an ultrafiltration, in which low-molecular components are separated by a hollow fiber membrane (H1 P3-20, Amicon). The aqueous product solution is filtered with a cellulose-membrane filter (pore size 0.45 μm, Sartorius) and freeze-dried.

Yield: 13.6 g (86.8% of theory) of colorless lyophilizate

Analysis (relative to the anhydrous substance): Cld: C 31.87 H 3.58 I 39.61 N 8.50 O 16.44 Fnd: C 31.98 H 3.68 I 39.43 N 8.62

Example 10

Production of the 3-(3-carboxypropionylamino)-5-(2,3-dihydroxypropylcarbamoyl)-2,4,6-triiodobenzoyl derivative of the 6-fold primary cascade amine [see example 10a)]

a) Tris-{[7,7-bis-(4,7-diaza-3-oxoheptyl)]-4,7-diaza-3-oxoheptyl}-amine (cascade amine with 6 primary amino groups)

127.0 g (121.6 mmol) of this cascade amine is produced according to U.S. Pat. No. 4,507,466 by reaction of nitrilotripropionic acid trimethyl ester (Pfaltz and Bauer) with 1. Ethylenediamine
2. methyl acrylate
3. ethylenediamine.

Analysis (relative to the anhydrous substance): Cld: C 51.75 H 8.98 N 25.48 O 13.79 Fnd: C 51.48 H 9.04 N 25.70 b) Production of the 3-(3-carboxypropionylamino)-5-(2,3-dihydroxypropylcarbamoyl)-2,4,6-triiodobenzoyl derivative of the 6-fold primary cascade amine [see example 10a)]

An emulsion consisting of 3.35 g (3.21 mmol) of the cascade amine produced under example 1b), 6.01 ml (43.3 mmol) of triethylamine and 30 ml of water is slowly instilled in a solution of 24.9 g (28.9 mmol) of the acid chloride, produced under example 1i), in 120 ml of N,N-dimethylformamide mechanically stirred at room temperature. The batch is stirred for 2 days at room temperature, then mixed with 60 ml of 2N sodium hydroxide solution and stirred for 2 hours at 50° C. After cooling to room temperature, the solution is neutralized with 2N hydrochloric acid and subjected to an ultrafiltration, in which low-molecular components are separated by a hollow fiber membrane (H1 P3-20, Amicon). The aqueous product solution is filtered with a cellose-membrane filter (pore size 0.45 μm, Sartorius and freeze-dried.

Yield: 15.0 g (76.2% of theory) of colorless lyophilizate

Analysis (relative to the anhydrous substance): Cld: C 30.43 H 3.24 I 42.87 N 8.15 O 15.31 Fnd: C 30.50 H 3.24 I 42.69 N 8.16

Example 11

Production of the 3-carboxymethylcarbamoyl-5-sodium carboxylatomethyl carbamoyl-2,4,6-triiodophenylthiocarbamoyl derivative of the 48-fold primary cascade amine [see example 1h)]

a) 5-Isothiocyanato-2,4,6-triiodoisophthalic acid-N,N'-bis-(methoxycarbonylmethyl)-diamide 20 ml of polyvinylpyridine (Reillex), 50 ml of water and 3.66 ml (49.4 mmol) of thiophosgene in 30 ml of 1,2-dichloroethane are added to a suspension of 17.3 g (24.7 mmol) of the aniline derivative, described under example 2a), in 170 ml of 1,2-dichloroethane stirred at room temperature. After 3 hours of stirring at 50° C., the batch is taken up in dichloromethane, the organic phase is separated, dried on anhydrous magnesium sulfate and filtered. The filtrate is concentrated by evaporation on a vacuum, the residue is absorptively precipitated with ethyl acetate, suctioned off and dried on a vacuum.

Yield: 16.6 g (90.7% of theory) of light beige solid

Analysis (relative to the solventless substance): Cld: C 24.25 H 1.63 I 51.24 N 5.66 O 12.92 S 4.32 Fnd: C 24.33 H 1.74 I 51.12 N 5.65 S 4.53 b) Production of the 3-carboxymethylcarbamoyl-5-sodium carboxylatomethylcarbamoyl-2,4,6-triiodophenylthiocarbamoyl derivative of the 48-fold primary cascade amine [see example 1h)]

A solution of 3.1 g (0.30 mmol) of the cascade amine, produced under example 1h), in 30 ml of dimethyl sulfoxide is instilled in a solution of 15.8 g (21.3 mmol) of the isothiocyanate, produced under example 11a), in 80 ml of dimethyl sulfoxide mechanically stirred at room temperature. The batch is stirred for 2 days at room temperature, then mixed with 30 ml of 2N sodium hydroxide solution and stirred for 2 hours at 50° C. After cooling to room temperature, the solution is neutralized with 2N hydrochloric acid and subjected to an ultrafiltration, in which low-molecular components are separated by a hollow fiber membrane (H1 P3-20, Amicon). The aqueous product solution is filtered with a cellulose-membrane filter (pore size 0.45 µm, Sartorius) and freeze-dried.

Yield: 12.1 g (88.0% of theory) of colorless lyophilizate

Analysis (relative to the anhydrous substance): Cld: C 28.33 H 2.76 I 39.91 N 10.03 Na 2.41 O 13.21 S 3.36 Fnd: C 28.45 H 2.99 I 39.69 N 10.20 Na 2.19 S 3.21

Example 12

Production of the 3-carboxymethylcarbamoyl-5-[(N-methoxy- acetyl)-methylamino]-2,4,6-triiodobenzoyl derivative of the 32-fold primary cascade amine [see example 12b)]

a) N-Methoxyacetyl-5-methylamino-2,4,6-triiodoisophthalic acid-N'-ethoxycarbonylmethyl-amide-chloride A solution of 68.2 g (100 mmol) of N-methoxyacetyl-5-methylamino-2,4,6-triiodoisophthalic acid dichloride (EP 0015867) in 500 ml of N,N-dimethylformamide is mixed with 14.0 g (100 mmol) of glycine ethyl ester hydrochloride (production according to D. A. Hoogwater, M. Peereboom, Tetrahedron, 46, 5325–5332 (1990)) and 10.1 g (100 mmol) of triethylamine. A suspension results, which is stirred overnight under argon at room temperature. Then, it is concentrated by evaporation, and the residue is chromatographed on silica gel 60 (Merck) with dichloromethane/ethyl acetate. After concentration by evaporation of the product fractions, a colorless solid is obtained, which is dried in a vacuum.

Yield: 53.4 g (71.49% of theory)

Analysis (relative to the solventless substance): Cld: C 25.68 H 2.15 Cl 4.74 I 50.87 N 3.74 O 12.83 Fnd: C 25.84 H 2.31 Cl4.62 I 50.59 N 3.69 b) Production of 3-carboxymethylcarbamoyl-5-[(N-methoxyacetyl)-methylamino]-2,4,6-triiodobenzoyl derivative of the 32-fold primary cascade amine.

A solution of 3.12 g (0.88 mmol) of cascade amine DAB (PA)$_4$(PA)$_8$(PA)$_{16}$(PA)$_{32}$ (WO 93/14147, example VIII) in 30 ml of water and 6.41 g (63.3 mmol) of triethylamine are simultaneously instilled in a solution of 31.6 g (42.2 mmol) of the acid chloride, produced under example 12a), in 200 ml of N,N-dimethylformamide mechanically stirred at room temperature under argon atmosphere. The batch is stirred for 2 days at room temperature, then mixed with 50 ml of 2N sodium hydroxide solution and stirred for 1.5 hours at 50° C. After the cooling to room temperature, the solution is neutralized with 2N hydrochloric acid and subjected to an ultrafiltration, in which low-molecular components are separated by a hollow fiber membrane (H1 P3-20, Amicon). The aqueous product solution is filtered with a cellulose-membrane filter (pore size 0.45 µm, Sartorius) and freeze-dried.

Yield: 18.7 g (83.7% of theory) of colorless lyophilizate

Analysis (relative to the anhydrous substance): Cld: C 29.88 H 3.11 I 47.96 N 6.95 O 12.09 Fnd: C 30.04 H 3.21 I 47.73 N 6.99

Example 13

Production of the 3-[(N-carboxymethyl)-sodium carboxylatomethylcarbamoyl]-5-[(N-methoxyacetyl)-methylamino]-2,4,6-triiodobenzoyl derivative of the 64-fold primary cascade amine [see example 13b)]

a) N-Methoxyacetyl-5-methylamino-2,4,6-triiodoisophthalic acid-N,N-bis-(ethoxycarbonylmethyl)-amide-chloride A solution of 68.2 g (100 mmol) of N-methoxyacetyl-5-methylamino-2,4,6-triiodoisophthalic acid dichloride (EP 0015867) in 500 ml of N,N-dimethylformamide is mixed with 22.6 g (100 mmol) of iminodiacetic acid diethyl ester hydrochloride (production according to Jongkees, Recl. Trav. Chimys-Bas, 27, 296 (1908)) and 10.1 g (100 mmol) of triethylamine. A suspension results, which is stirred overnight under argon at room temperature. Then, it is concentrated by evaporation and the residue is chromatographed on silica gel 60 (Merck) with dichloromethane/ethyl acetate. After concentration by evaporation of the product fractions, a colorless solid is obtained, which is dried in a vacuum.

Yield: 61.3 g (76.0% of theory)

Analysis (relative to the solventless substance): Cld: C 26.81 H 2.25 Cl 4.40 I 47.21 N 3.47 O 15.87 Fnd: C 26.79 H 2.32 Cl 4.43 I 47.15 N 3.52 b) Production of the 3-[(N-carboxymethyl)-sodium carboxylatomethylcarbamoyl]-5-[(N-methoxyacetyl)-methylamino]-2,4,6-triiodobenzoyl derivative of the 64-fold primary cascade amine.

A solution of 5.54 g (0.77 mmol) of cascade amine DAB (PA)$_4$(PA)$_8$(PA)$_{16}$(PA)$_{32}$(PA)$_{64}$ (WO 93/14147, example X) in 50 ml of water and 15.4 ml (111 mmol) of triethylamine are simultaneously instilled in a solution of 59.8 g (74.1 mmol) of the acid chloride, produced under example 13a), in 200 ml of N,N-dimethylformamide mechanically stirred at room temperature under argon atmosphere. The batch is stirred for 2 days at room temperature, then mixed with 100 ml of 2N sodium hydroxide solution and stirred for 2 hours at 50° C. After cooling to room temperature, the solution is neutralized with 2N hydrochloric acid, and subjected to an ultrafiltration, in which low-molecular components are separated by a hollow fiber membrane (H1 P3-20, Amicon). The aqueous product solution is filtered with a cellulose-membrane filter (pore size 0.45 µm, Sartorius) and freeze-dried.

Yield: 40.4 g (93.2% of theory) of colorless lyophilizate

Analysis (relative to the anhydrous substance): Cld: C 29.99 H 2.96 I 43.46 N 6.35 O 14.61 Na 2.62 Fnd: C 30.27 H 3.19 I 43.18 N 6.48 Na 2.36

Example 14

Production of the 2-{3-[(N-carboxymethyl)-methylcarbamoyl]-5-[(N-sodium carboxylatomethyl)-methylcarbamoyl]- 2,4,6-triiodophenylcarbamoyl}-ethyl derivative of the 24-fold primary cascade amine [see example 1f)]

a) 5-Acrylamido-2,4,6-triiodoisophthalic acid-N,N'-bis-(ethoxycarbonyl)-N,N'-dimethyl-diamide 8.7 g of the aniline derivative, produced under example 4a), in 45 ml of N,N-dimethylacetamide is mixed at 0° C. with 3.12 g (34.5 mmol) of distilled acrylic acid chloride. The reaction mixture is stirred for 18 hours at room temperature and then poured in ice water. The resulting precipitate is suctioned off and washed neutral with water. The crude product is dried in a vacuum at 50° C. and purified by an HPLC (stationary phase: RP18, mobile phase: water/acetonitrile). After the concentration by evaporation of the product fractions, the residue is foamed in a high vacuum.

Yield: 7.4 g (79% of theory) of colorless solid.

Analysis (relative to the anhydrous substance): Cld: C 31.09 H 2.98 I 46.94 N 5.18 O 13.81 Fnd: C 30.96 H 3.18 I 46.72 N 5.04 b) Production of the 2-{3-[(N-carboxymethyl)-methylcarbamoyl]-5-[(N-sodium carboxylatomethyl)-methylcarbamoyl]-2,4,6-triiodophenylcarbamoyl}-ethyl derivative of the 24-fold primary cascade amine [see example 1f)]

0.895 g (0.18 mmol) of polyamine (example 1f) is added to a solution of 7.05 g (8.7 mmol) of acrylamide of example 14a) in 25 ml of N,N-dimethylformamide at room temperature, and the reaction mixture is stirred at 75° C. for 5 hours. After completion of the reaction, the batch is evaporated to dryness in a vacuum and mixed with 2n sodium hydroxide solution for 2 hours at 50° C. When saponification has taken place, the solution is neutralized and ultrafiltered for separation of low-molecular components with a hollow fiber membrane (H1 P3-20, Amicon). The aqueous product solution is filtered with a cellulose-membrane filter (pore size 0.45 μm) and freeze-dried.

Yield: 6.85 g (92% of theory) of colorless lyophilizate.

Analysis (relative to the anhydrous substance): Cld: C 30.03 H 1.83 I 44.28 N 7.87 O 14.65 Na 1.34 Fnd: C 29.87 H 1.97 I 44.19 N 7.61 Na 1.16

Example 15

Production of the N-methoxyacetyl-3-methylamino-5-(2-sulfoethylcarbamoyl)-2,4,6-triiodobenzoyl derivative of the 48-fold primary cascade amine [see example 1h)]

a) N-Methoxyacetyl-5-methylamino-2,4,6-triiodoisophthalic acid-N'-(2-bromoethyl)-amide-chloride A solution of 68.2 g (100 mmol) of N-methoxyacetyl-5-methylamino-2,4,6-triiodoisophthalic acid dichloride (EP 0 015 867) in 500 ml of N,N-dimethylformamide is mixed with 20.5 g (100 mmol) of 2-bromoethylamine-hydrobromide and 20.2 g (200 mmol) of triethylamine. A suspension results, which is stirred overnight under argon at room temperature. Then, it is concentrated by evaporation and the residue is chromatographed on silica gel 60 (Merck) with dichloromethane/ethyl acetate. After concentration by evaporation of the product fractions, a colorless solid is obtained, which is dried in a vacuum.

Yield: 55.3 g (71.88% of theory)

Analysis (relative to the solventless substance): Cld: C 21.86 H 1.70 Br 10.39 Cl 4.61 I 49.49 N 3.64 O 8.32 Fnd: C 21.84 H 1.81 Br 10.48 Cl 4.62 I 49.59 N 3.69 b) Production of the N-methoxyacetyl-3-methylamino-5-(2-bromoethylcarbamoyl)-2,4,6-triiodobenzoyl derivative of the 48-fold primary cascade amine [see example 1b)]

A solution of 10.1 g (0.97 mmol) of the cascade amine, described in example 1b), in 50 ml of water and 12.6 ml (90.9 mmol) of triethylamine are simultaneously instilled in a solution of 53.8 g (69.9 mmol) of the acid chloride, produced under example 15a), in 200 ml of N,N-dimethylformamide mechanically stirred at room temperature under argon atmosphere. The batch is stirred for 2 days at room temperature, then neutralized with 2N hydrochloric acid and subjected to an ultrafiltration, in which low-molecular components are separated by a hollow fiber membrane (H1 P3-20, Amicon). The aqueous product solution is filtered with a cellulose-membrane filter (pore size 0.45 μm, Sartorius) and freeze-dried.

Yield: 39.5 g (89.2% of theory) of colorless lyophilizate

Analysis (relative to the anhydrous substance): Cld: C 29.71 H 3.30 Br 8.41 I 40.08 N 8.60 O 9.90 Fnd: C 29.83 H 3.37 Br 8.52 I 39.90 N 8.55 c) Production of the N-methoxyacetyl-3-methylamino-5-(2-sulfoethylcarbamoyl)-2,4,6-triiodobenzoyl derivative of the 48-fold primary cascade amine [see example 1h)]

37.4 g (0.82 mmol) of the compound described in example 15b) is mixed in 500 ml of water with 49.6 g (393 mmol) of sodium sulfite and stirred for 72 hours at 25° C. Then, the aqueous solution is subjected to an ultrafiltration, in which low-molecular components are separated by a hollow fiber membrane (H1 P3-20, Amicon). The aqueous product solution is filtered with a cellulose-membrane filter (pore size 0.45 μm, Sartorius) and freeze-dried.

Yield: 31.2 g (83.2% of theory) of colorless lyophilizate

Analysis (relative to the anhydrous substance): Cld: C 29.66 H 3.40 I 40.00 N 8.58 O 14.99 S 3.37 Fnd: C 29.73 H 3.47 I 39.91 N 8.65 S 3.22

Example 16

Production of the 3,5-di-(sodium phosphonomethylcarbamoyl)-2,4,6-triiodoarylcarbamoyl derivative of the 12-fold primary cascade amine [see example 1d)]

a) 5-Amino-2,4,6-triiodoisophthalic acid-N,N'-bis-(diethylphosphonomethyl)-diamide A solution of 59.6 g (100 mmol) of 5-amino-2,4,6-triiodoisophthalic acid dichloride (DOS 29 26 428) in 300 ml of N,N-dimethylformamide is mixed with 36.8 g (220 mmol) of aminomethanephosphonic acid diethyl ester and 61.0 ml (440 mmol) of triethylamine. A suspension results, which is stirred overnight at room temperature under argon. After the concentration by evaporation of the suspension in a vacuum, the residue is recrystallized from methanol.

Yield: 59.8 g (69.8% of theory)

Analysis (relative to the solventless substance): Cld: C 25.22 H 3.29 I 44.42 N 4.90 P 7.23 O 14.93 Fnd: C 25.16 H 3.41 I 44.26 N 4.78 P 7.17 b) 5-Isocyanato-2,4,6-triiodoisophthalic acid-N,N'-bis-(diethylphosphonomethyl)-diamide 147 ml (73.8 mmol) of a 2N toluenic phosgene solution and 2 ml of N,N-dimethylformamide are added to a suspension of 25.7 g (30 mmol) of the aniline derivative, produced under example 16a), in 200 ml of 1,2-dichloroethane stirred at 65° C. oil bath temperature under argon atmosphere. After completion of the reaction of the aniline derivative, the batch is concentrated by evaporation in a vacuum, the residue is absorptively precipitated with anhydrous ethyl acetate, suctioned off under nitrogen atmosphere and dried in an oil pump vacuum.

Yield: 25.6 g (96.7% of theory) of light beige solid

Analysis (relative to the solventless substance): Cld: C 25.84 H 2.97 I 43.11 N 4.76 P 7.02 O 16.31 Fnd: C 25.72 H 3.08 I 42.98 N 4.59 P 6.91 c) Production of the 3,5-di-(sodium phosphonomethylcarbamoyl)-2,4,6-triiodoarylcarbamoyl derivative of the 12-fold primary cascade amine [see example 1d)]

A solution of 4.68 g (2.12 mmol) of the cascade amine, produced under example 1d), in 47 ml of anhydrous dimethyl sulfoxide is slowly instilled in a solution of 22.5 g (25.5 mmol) of the isocyanate, produced under example 16b), in 220 ml of anhydrous dimethyl sulfoxide stirred at room temperature under argon atmosphere. The batch is stirred for 3 days at room temperature, then concentrated by evaporation in a high vacuum, mixed with 14.11 ml (110.5 mmol) of bromotrimethylsilane and stirred for 26 hours at 45° C. The crude product is mixed drop by drop with 150 ml of water and stirred for 4 hours at room temperature. After neutralization with sodium hydroxide solution, the product solution is subjected to an ultrafiltration, in which low-molecular components are separated by a hollow fiber membrane (H1 P3-20, Amicon). The aqueous product solution is filtered with a cellulose-membrane filter (pore size 0.45 µm, Sartorius) and freeze-dried.

Yield: 19.98 g (78.7% of theory) of yellowish lyophilizate.

Analysis (relative to the anhydrous substance): Cld: C 22.86 H 2.47 I 38.14 N 8.89 Na 4.61 P 6.21 O 16.83 Fnd: C 22.69 H 2.61 I 38.03 N 8.65 Na 4.49 P 6.08

Example 17

Production of the triacontakis-{3-(4-carboxy-3-oxabutyrylamino)-5-(2,3-dihydroxypropylcarbamoyl)-2,4,6-triiodobenzoyl}-bis-(4-carboxy-3-oxabutyryl) derivative of the 32-fold primary cascade amine [see example 12]

A solution of 5.53 g (1.56 mmol) of cascade amine DAB $(PA)_4(PA)_8(PA)_{16}(PA)_{32}$ [WO 93/14147, example VIII] in 40 ml of water and 13.9 ml (100 mmol) of triethylamine are simultaneously instilled in a solution of 44.6 g (50.0 mmol) of the acid chloride, produced under example 6b), in 250 ml of N,N-dimethylformamide mechanically stirred at room temperature under argon atmosphere. The batch is stirred for 2 days at room temperature, then mixed with 1.16 g (10.0 mmol) of diglycolic anhydride and stirred for another 24 hours. Then, 50 ml of 2N sodium hydroxide solution is added and stirred for 1.5 hours at 50° C. After the cooling to room temperature, the solution is neutralized with 2N hydrochloric acid and subjected to an ultrafiltration, in which low-molecular components are separated by a hollow fiber membrane (H1 P3-20, Amicon). The aqueous product solution is filtered with a cellulose-membrane filter (pore size 0.45 µm, Sartorius) and freeze-dried.

Yield: 35.6 g (88.8% of theory) of colorless lyophilizate

Analysis (relative to the anhydrous substance): Cld: C 30.03 H 3.26 I 44.49 N 6.76 O 15.45 Fnd: C 30.14 H 3.21 I 44.43 N 6.69

Example 18

Production of the 3-(4-carboxy-3-oxabutyrylamino)-5-(2,3,4,5,6-pentahydroxyhexyl-carbamoyl)-2,4,6-triiodobenzoyl derivative of the 48-fold primary cascade amine [see Example 1h)]

a) 3-Amino-5-(2,3,4,5,6-pentaacetoxyhexylcarbamoyl)-2,4,6-triiodobenzoic acid 14.7 g (20 mmol) of 3-amino-5-(2,3,4,5,6-pentahydroxyhexylcarbamoyl)-2,4,6-triiodobenzoic acid (DOS 1928838) is dissolved in 30 ml of N,N-dimethylacetamide and mixed with 25 mg of 4-(dimethylamino)-pyridine at room temperature. It is cooled to 0° C. and 11.3 ml (120 mmol) of acetic anhydride is added within 30 minutes drop by drop. After another 30 minutes at this temperature, it is allowed to reach room temperature overnight. The excess acetic anhydride is reacted with methanol and the reaction mixture is concentrated by evaporation. The residue is taken up in 100 ml of butyl acetate and washed successively with sodium bicarbonate solution and saturated sodium chloride solution. After the drying of the organic phase on sodium sulfate, the solution is evaporated to dryness. The crude product can be used in the next stage without further purification.

Yield: 16.2 g (85.6% of theory) of yellowish foam.

b) 3-Amino-5-(2,3,4,5,6-pentaacetoxyhexylcarbamoyl)-2,4,6-triiodobenzoic acid chloride 15.5 g (16.4 mmol) of 3-amino-5-(2,3,4,5,6-pentaacetoxyhexylcarbamoyl)-2,4,6-triiodobenzoic acid [Example 18a)] is suspended in 80 ml of ethyl acetate and refluxed with 1.9 ml (24.6 mmol) of thionyl chloride for 5 hours. The reaction mixture is added to 30 g of sodium bicarbonate in 300 ml of water and stirred vigorously for 1.5 hours. Then, the phases are separated and the organic phase is dried on sodium sulfate, filtered, and the solution is concentrated by evaporation. The oily reaction product is foamed up in a high vacuum.

Yield: 14.9 g (94% of theory) of light yellow foam.

Analysis (relative to the solventless substance): Cld: C 31.13 H 2.93 Cl 3.68 I 39.47 N 2.90 O 19.90 Fnd: C 31.35 H 3.06 Cl 3.52 I 39.28 N 2.74 c) 5-[4-(2-Methylethyloxycarbonyl)-3-oxabutyrylamino]-5-(2,3,4,5,6-pentaacetoxyhexylcarbamoyl)-2,4,6-triiodobenzoic acid chloride 3.9 g (20 mmol) of the acid chloride produced according to Example 6a) is added at room temperature to a suspension of 12.9 g (13.3 mmol) of 3-amino-5-(2,3,4,5,6-pentaacetoxyhexylcarbamoyl)-2,4,6-triiodobenzoic acid chloride [Example 18b)] in 50 ml of anhydrous dioxane, stirred with exclusion of moisture. The batch is refluxed for 6 hours, until no more feedstock can be detected according to thin-layer chromatography, then it is concentrated by evaporation, the residue is taken up in dichloromethane and shaken out with saturated, aqueous sodium bicarbonate solution. After drying on anhydrous magnesium sulfate, the organic phase is concentrated by evaporation and the residue is recrystallized from ethyl acetate/tert-butyl methyl ether.

Yield: 11.3 g (75.7% of theory) of colorless crystals.

Analysis (relative to the solventless substance): Cld: C 34.23 H 3.41 Cl 3.16 I 33.91 N 2.50 O 22.80 Fnd: C 34.45 H 3.53 Cl 3.12 I 33.80 N 2.34 d) 3-(4-Carboxy-3-oxabutyrylamino)-5-(2,3,4,5,6-pentahydroxyhexylcarbamoyl)-2,4,6-triiodobenzoyl derivative of the 48-fold primary cascade amine [see Example 1h)]

An emulsion consisting of 1.4 g (0.13 mmol) of the cascade amine produced under Example 1h), 2.0 ml (15.0 mmol) of triethylamine and 10 ml of water is slowly instilled in a solution of 10.8 g (9.6 mmol) of the acid chloride, produced under Example 18c), in 40 ml of N,N-dimethylformamide, mechanically stirred at room temperature. The batch is stirred for 2 days at room temperature, then mixed with 20 ml of 2N sodium hydroxide solution and stirred for 2 hours at 50° C. After cooling to room temperature, the solution is neutralized with 2N hydrochloric acid and then subjected to an ultrafiltration, and low-molecular components are separated by a hollow fiber membrane (H1 P3-20, Amicon). The aqueous product solution is filtered with a cellulose-membrane filter (pore size 0.45 µm, Sartorius) and freeze-dried.

Yield: 5.4 g (82.3% of theory) of colorless lyophilizate.

Analysis (relative to the anhydrous substance): Cld: C 32.57 H 3.85 I 36.22 N 7.77 O 19.60 Fnd: C 32.34 H 3.97 I 36.13 N 7.52

Example 19

Production of the 3-(2,3-dihydroxy-3-carboxypropionylamino)-5-(2,3-dihydroxy-propylcarbamoyl)-2,4,6-triiodobenzoyl derivative of the 48-fold primary cascade amine [see Example 1h)]

a) 5-(2,3-Diacetoxy-3-methoxycarbonylpropionylamino)-2,4,6-triiodoisophthalic acid-N-(2,3-diacetoxypropyl)amide-chloride 17.58 g (70.87 mmol) of O,O-diacetyltartaric acid monomethyl ester and 7.71 ml (106.3 mmol) of thionyl chloride are added at room temperature to a suspension of 25.37 g (35.43 mmol) of 5-amino-2,4,6-triiodoisophthalic acid-N-(2,3-diacetoxypropyl)-amide (EP 0 308 364) in 150 ml of ethyl acetate, stirred with exclusion of moisture. The batch is refluxed for several hours, until the reaction according to thin-layer chromatography is complete; then it is concentrated by evaporation, the residue is taken up in dichloromethane and shaken out with saturated aqueous sodium bicarbonate solution. After drying on anhydrous magnesium sulfate, the organic phase is concentrated by evaporation and the residue is chromatographed on silica gel with dichloromethane/ethyl acetate.

Yield: 25.57 g (74.81% of theory)

Analysis (relative to the solventless substance): Cld: C 29.88 H 2.51 Cl 3.68 I 39.47 N 2.90 O 21.56 Fnd: C 29.94 H 2.63 Cl 3.81 I 39.30 N 2.82 b) 3-(2,3-Dihydroxy-3-carboxypropionylamino)-5-(2,3-dihydroxypropylcarbamoyl)-2,4,6-triiodobenzoyl derivative of the 48-fold primary cascade amine [see Example 1h)]

An emulsion, consisting of 3.84 g (0.37 mmol) of the cascade amine produced under Example 1h), 5.51 ml (39.8 mmol) of triethylamine and 30 ml of water, is slowly instilled in a solution of 25.6 g (26.5 mmol) of the acid chloride, produced under Example 19a), in 100 ml of N,N-dimethylformamide, mechanically stirred at room temperature. The batch is stirred for 2 days at room temperature, then mixed with 50 ml of 2N sodium hydroxide solution and stirred for 2 hours at 50° C.; after cooling to room temperature, the solution is neutralized with 2N hydrochloric acid and subjected to an ultrafiltration, and low-molecular components are separated by a hollow fiber membrane (H1 P3-20, Amicon). The aqueous product solution is filtered with a cellulose-membrane filter (pore size 0.45 μm, Sartorius) and freeze-dried.

Yield: 14.7 g (86.3% of theory) of colorless lyophilizate

Analysis (relative to the solventless substance): Cld: C 30.56 H 3.36 I 39.53 N 8.48 O 18.07 Fnd: C 30.69 H 3.42 I 39.40 N 8.55

Despite administration of the same dose, the blood concentration of Ultravist® decreases much more quickly than the concentration of the polymer according to example 1j. This can be attributed to the quick distribution of Ultravist® from the blood space to the interstitial space, while the distribution of the polymer according to example 1j is limited to the blood space.

Figure 1:
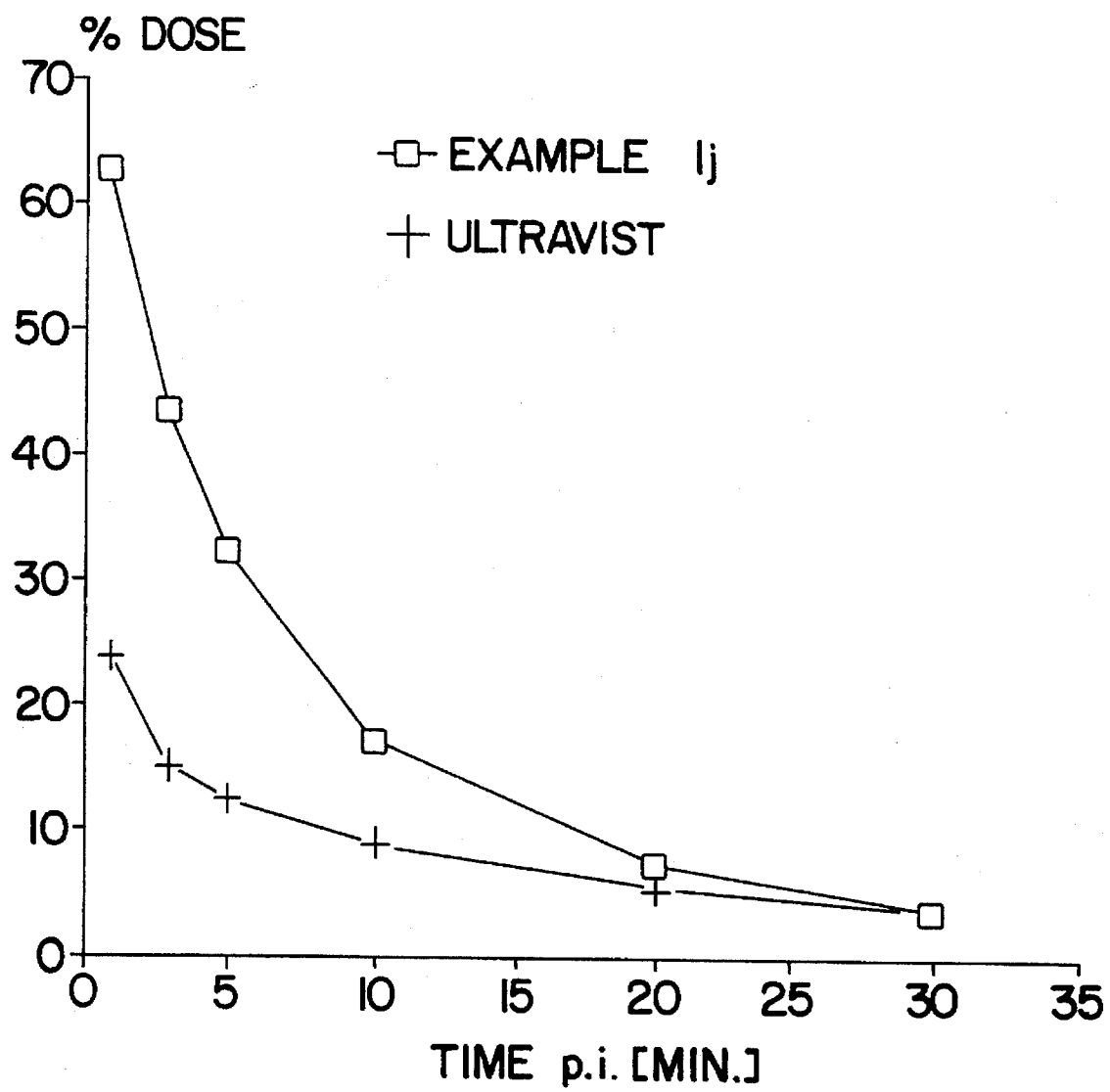
FIG. 1 illustrates blood level as a function of time in rats after one-time intravenous injection of 300 mg of I/kg of body weight of Ultravist® and the compound according to example 1j. The data represent the average value of four animals each.
Figure 2:
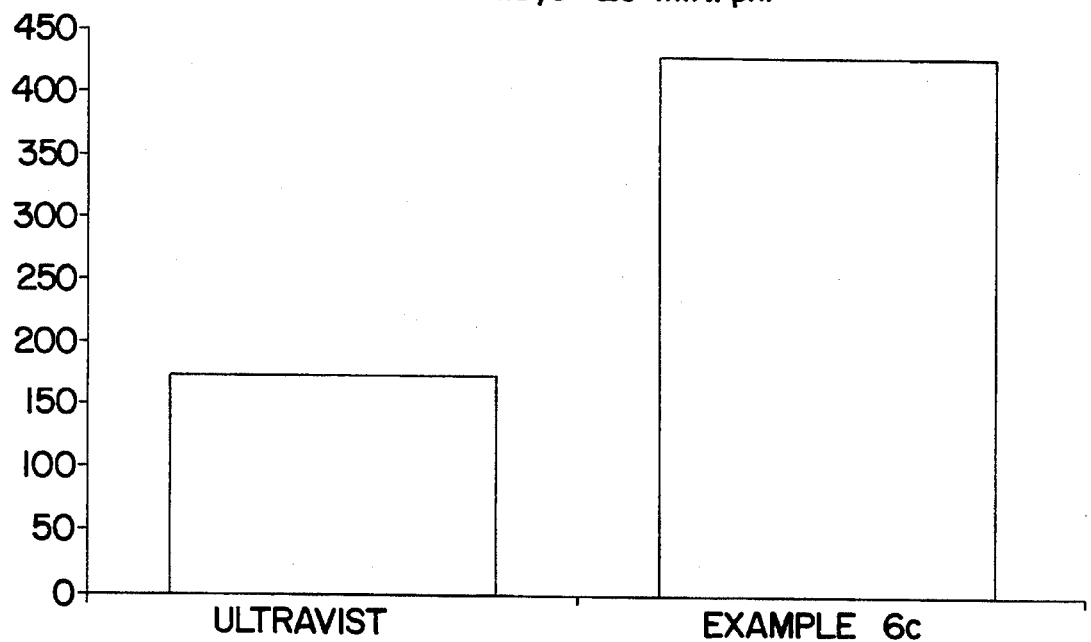

FIG. 2 shows the signal data in vivo imaging of both the monomeric X-ray contrast medium Ultravist® (iopromide) and the compound of Example 6c (macromolecule) administered with a dose of 200 mg 1/kg intravenously in a bolus to a rabbit (2 kg White New Zealander) (n=1 per substance). From 0 to 20 minutes after administration, the signal increase was measured in Hounsfield units (HU) in the liver parenchyma and in the aorta. For this purpose, a spiral-CT (Somatom plus) of the Siemens company was used. The recordings were made at 120 kV. The signal-time curve in the aorta and in the liver was measured for both substances. The area under the curves was calculated in (AUD=area under the data). The signal difference between aorta and liver parenchyma over the period of 0–20 minutes was used (AUD aorta—AUD liver) as a measurement for the contrast quality of the substances.

The figure clearly shows that the signal difference between the blood vessel (aorta) and the surrounding liver tissue is clearly higher for the compound of Example 6c (macromolecule) than in the case of the monomer Ultravist.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An iodine-containing dendrimeric polymer of general formula I $$A\text{---}(X)_b \qquad (I),$$

wherein

A is a nitrogen-containing nucleus of basic multiplicity b;

b is a number from 1 to 8;

X is a radical composed of $$\sum_{k=0}^{n-1} 2^k$$

reproduction units S having at most $2^n$ imaging radicals Z;

n represents the number of generations and is a number from 1 to 10;

S is a radical of formula II

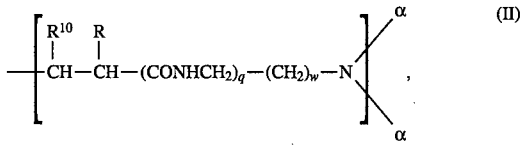

R and $R^{10}$, independently of one another, are each a hydrogen atom or a methyl group, w is 1 or 2, q is 0 or 1, and positions α for each generation up to n−1 is, in each case, occupied by a further reproduction unit S, and for n-th generation is in each case, occupied by a radical Z or by radical —(CO)$_q$—U—COOH, in which q has the above-indicated meaning and U stands for a direct bond or an alkylene chain with up to 6 C atoms, which is optionally interrupted by 1–2 oxygen atoms and/or optionally substituted by 1–4 hydroxy groups and/or 1–2 carboxy groups, provided that at most 20% of positions α in the n-th generation are occupied by —(CO)$_q$—U—COOH;

Z is an imaging radical Y—B, which contains at least one aliphatic carboxy, aliphatic sulfo or aliphatic phosphono group, and is made up of a linking element Y and a triiodoaromatic group B;

Y is —CO—, —CONH— —CSNH—,

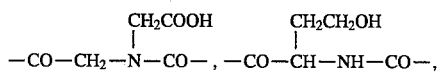

—CHR—CHR—CONH— or

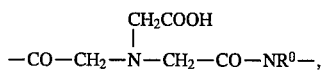

wherein R has the above-mentioned meaning;
R⁰ is a hydrogen atom, methyl or carboxymethyl;
B is a benzene ring of the formula

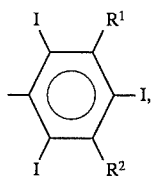

$R^1$ and $R^2$, independently of one another, are each a hydrogen atom, —$CONR^3R^4$ or —$NR^6COR^5$;

$R^3$ and $R^4$, independently of one another, are each a hydrogen atom, a straight-chain or branched-chain or cyclic alkyl group with up to 12 C atoms optionally substituted by 1–5 hydroxy and/or 1–3 $C_1$–$C_3$ alkoxy and/or 1–3 carboxy, sulfo or phosphono group(s), or $R^3$ and $R^4$ together with the nitrogen atom, are a 5- or 6-membered ring optionally containing an oxygen atom, $SO_2$ group or N—CO—$R^7$;

$R^7$ is a carboxy group or an alkyl group with up to 12 C atoms optionally containing 1–5 hydroxy, 1–3 $C_1$–$C_3$ alkoxy or 1–3 carboxy, sulfo or phosphono group(s);

$R^5$ is a carboxy group, an alkyl group with up to 12 C atoms optionally interrupted by an oxygen atom and/or optionally substituted by 1–3 carboxy, sulfo or phosphono and/or 1–5 hydroxy and/or 1–3 $C_1$–$C_3$ alkoxy group(s); and $R^6$ is a hydrogen atom, an alkyl group with up to 12 C atoms optionally substituted by 1–3 carboxy, sulfo or phosphono group(s) and/or optionally substituted by 1–3 hydroxy group(s) and/or 1–3 $Ch_1$–$C_3$ alkoxy groups;

wherein reproduction units S must be identical only within a generation;
or a physiologically acceptable salt thereof with organic and/or inorganic bases, amino acids or amino acid amides.

2. An iodine-containing dendrimeric polymer according to claim 1, wherein nucleus A is a nitrogen atom, β-$NR^8$-β, β-$NR^8R^9$ or a group of formulae III, IV, V or VI,

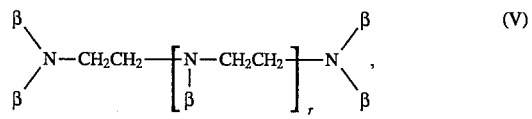

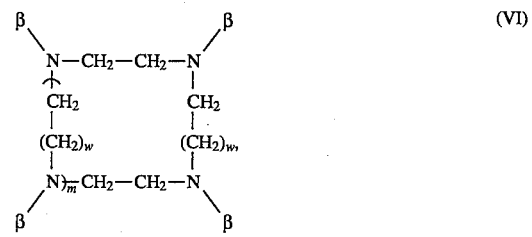

wherein
$R^8$ and $R^9$, independently of one another, are each a straight-chain or branched alkyl, aryl or aralkyl radical with up to 20 C atoms, which optionally is substituted by 1–4 hydroxy group(s);

β is the binding site to a group X wherein the number of β's is equated to basic multiplicity b;

V is a straight-chain or branched alkylene, arylene or aralkylene radical with up to 20 C atoms, which optionally is interrupted by 1–4 oxygen atom(s) and/or substituted by 1–4 hydroxy group(s);

r is 1, 2 or 3;
w is 1 or 2; and
m is 0, 1, 2 or 3.

3. An iodine-containing dendrimeric polymer according to claim 1, wherein nucleus A is $β_2N$-$(CH_2)_4$-$Nβ_2$, $β_2N(CH_2)_2Nβ_2$, $βN(CH_2CH_2Nβ_2)_2$, $N(CH_2CH_2Nβ_2)_3$,

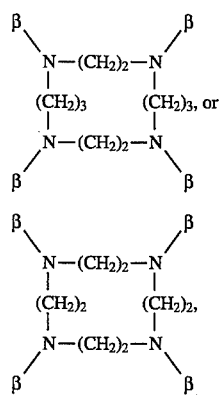

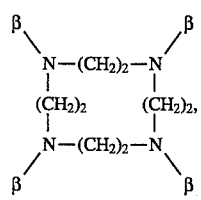

wherein β is the binding site to a group X wherein the number of β's is equated to basic multiplicity b.

4. An iodine-containing dendrimeric polymer according to claim 1, wherein S is

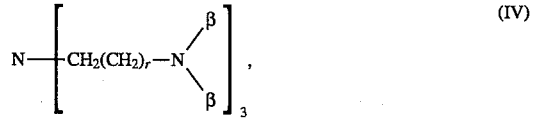

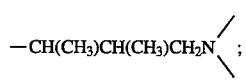

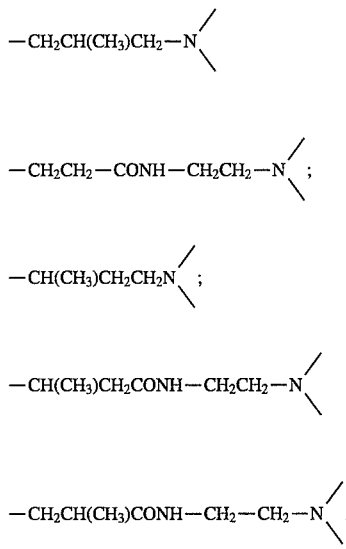

5. An iodine-containing dendrimeric polymer according to claim 1, wherein n is 2–6.

6. An iodine-containing dendrimeric polymer according to claim 1, wherein $R^1$ or $R^2$ is —$CONH_2$, —$CONHCH_2COOH$, —$CON(CH_2COOH)_2$, —$CONHCH_2CH(OH)CH_2OH$, —$CON(CH_3)CH_2COOH$, —$CONHCH_2PO_3H_2$, —$CON(CH_2PO_3H_2)_2$, —$CON(CH_2COOH)CH_2PO_3H_2$, —$CON(CH_3)CH_2CH(OH)CH_2OH$, —$CONHCH_2CH_2SO_3H$, or —$CON(CH_2CH_2SO_3H)_2$.

7. An iodine-containing dendrimeric polymer according to claim 1, wherein $R^1$ or $R^2$ is —$NHCO(CH_2)_2$—$COOH$, —$NHCOCOOH$, —$NHCOCH_2OCH_2COOH$, —$NHCOCH_2OCH_3$, —$N(CH_2COOH)COCH_2OCH_3$, —$NHCOCH_3$, or —$N(CH_3)COCH_2OCH_3$.

8. An iodine-containing dendrimeric polymer according to claim 1, wherein V is —$(CH_2)_4$—, —$CH_2$—$C_6H_4$—$CH_2$—, —$(CH_2)_2$—, —$(CH_2)_2$—O—$(CH_2)_2O(CH_2)_2$—, —$CH_2CHOHCH_2$—, or —$(CH_2)_2$—O—$(CH_2)_2$—.

9. An iodine-containing dendrimeric polymer according to claim 1, wherein —$(CO)_q$—U—COOH is —$CO(CH_2)_2$—COOH, —COCOOH, —$CO(CHOH)_2$—COOH, —$COCH_2OCH_2COOH$, —$COCH_2COOH$, —$COCH(OCH_3)COOH$, or —$CH_2CH_2COOH$.

10. A process for production of iodine-containing dendrimeric polymers according to claim 1, comprising:

reacting a dendrimeric polymer of general formula I'

in which

A and b have the meaning indicated in claim 1, and

X' has the meaning indicated for X in claim 1, but unlike X for the n-th generation, positions α are not occupied by radicals Z or —$(CO)_q$—U—COOH, but by hydrogen atoms, with a compound of general formula II

in which

Y' is a radical to be converted to Y containing a carbonyl, thiocarbonyl, activated carbonyl or a CHR=CR group, wherein R is a hydrogen atom or a methyl group; and B' has the meaning of a triiodoaromatic compound indicated for B, and carboxy and hydroxy groups contained in B are, however, present in protected form; and then positions α not occupied by radicals Z are optionally acylated or alkylated with a reagent introducing radical —$(CO)_q$—U—COOH.

11. A diagnostic composition comprising an effective amount of at least one iodine-containing dendrimeric polymer according to claim 1 and a physiologically compatible medium.

12. A method of performing X-ray diagnosis of vascular disease of a patient, said method comprising X-ray imaging a patient to whom at least one iodine-containing dendrimeric polymer according to claim 1 has been administered.

13. A method of enhancing an X-ray diagnostic image comprising administering to a patient an iodine-containing dendrimeric polymer according to claim 1.

14. An iodine-containing dendrimeric polymer according to claim 1, wherein said polymer exhibits a molecular weight of 10,000–500,000.

15. An iodine-containing dendrimeric polymer according to claim 1, wherein said polymer exhibits a molecular weight of 20,000–100,000.

16. An iodine-containing dendrimeric polymer according to claim 1, wherein b is 1 to 6.

17. An iodine-containing dendrimeric polymer according to claim 1, wherein $R^3$ is a straight- or branched-chain or cyclic hydrocarbon having up to 10 C atoms which is optionally substituted by 1–3 hydroxy and/or 1–3 $C_1$–$C_3$ alkoxy and/or 1 carboxy, sulfo or phosphono group.

18. An iodine-containing dendrimeric polymer according to claim 1, wherein $R^4$ is a straight- or branched-chain or cyclic hydrocarbon having up to 10 C atoms which is optionally substituted by 1–3 hydroxy and/or 1–3 $C_1$–$C_3$ alkoxy and/or 1 carboxy, sulfo or phosphono group.

19. An iodine-containing dendrimeric polymer according to claim 1, wherein $R^3$ and $R^4$, together with the nitrogen atom, are piperidyl, pyrazolidyl, morpholinyl, piperazinyl substituted by —CO—$R^7$ or S,S-dioxothiomorpholinyl.

20. An iodine-containing dendrimeric polymer according to claim 9, wherein —$(CO)_q$—U—COOH is —$CO(CH_2)_2COOH$, —$COCH_2OCH_2COOH$ or —$CH_2CH_2COOH$.

21. An iodine-containing dendrimeric polymer according to claim 1, wherein U is an alkylene chain of up to 2 C atoms optionally interrupted by 1–2 oxygen atoms and/or optionally substituted by 1–2 hydroxy groups and/or 1–2 carboxy groups.

22. A composition according to claim 11, wherein the iodine content of said composition is 50–450 mg/ml.

23. A composition according to claim 22, wherein the iodine content of said composition is 70–200 mg/ml.

24. A method according to claim 13, wherein said polymer is administered to said patient in a dose of 30–200 mg of iodine per kg.

25. A composition according to claim 11, said composition further comprising at least one physiologically harmless buffer, at least one stabilizer, at least one electrolyte, at least one antioxidant, at least one osmolality matching substance or mixtures thereof.

26. An iodine-containing dendrimeric polymer according to claim 1, wherein said polymer is a 48-fold primary cascade amine.

27. An iodine-containing dendrimeric polymer according to claim 26, wherein said polymer is:

3-(3-Carboxypropionylamino)-5-(2,3-dihydroxypropylcarbamoyl)-2,4,6-triiodobenzoyl derivative of 48-fold primary cascade amine;

3-carboxymethylcarbamoyl-5-sodium carboxylatomethylcarbamoyl-2,4,6-triiodophenylcarbamoyl derivative of 48-fold primary cascade amine;

3,5-bis-[(N-carboxymethyl)-sodium carboxylatomethylcarbamoyl]-2,4,6-triiodophenylcarbamoyl derivative of 48-fold primary cascade amine;

3-[(N-carboxymethyl)-methylcarbamoyl]-5-[(N-sodium carboxylatomethyl)-methylcarbamoyl]-2,4,6-triiodophenylcarbamoyl derivative of 48-fold primary cascade amine;

3-carboxyformylamino-5-(2,3-dihydroxypropylcarbamoyl)-2,4,6-triiodobenzoyl derivative of 48-fold primary cascade amine;

3-(4-carboxy-3-oxabutyrylamino)-5-(2,3-dihydroxypropylcarbamoyl)-2,4,6-triiodobenzoyl derivative of 48-fold primary cascade amine;

3-[(N-carboxymethyl)-sodium carboxylatomethylcarbamoyl]-5-methoxy-acetylamino-2,4,6-triiodobenzoyl derivative of 48-fold primary cascade amine;

N-[3,5-di-(acetylamino)-2,4,6-triiodobenzoyl]-N-(carboxymethyl)-glycyl derivative of 48-fold primary cascade amine;

3-[(N-carboxymethyl)-methoxyacetylamino]-5-(2,3-dihydroxy-propylcarbamoyl)-2,4,6-triiodobenzoyl derivative of 48-fold primary cascade amine;

3-(3-carboxypropionylamino)-5-(2,3-dihydroxypropylcarbamoyl)-2,4,6-triiodobenzoyl derivative of 48-fold primary cascade amine;

3-carboxymethylcarbamoyl-5-sodium carboxylatomethylcarbamoyl-2,4,6-triiodophenylthiocarbamoyl derivative of 48-fold primary cascade amine;

3-carboxymethylcarbamoyl-5-[(N-methoxyacetyl)-methylamino]-2,4,6-triiodobenzoyl derivative of 48-fold primary cascade amine;

3-[(N-carboxymethyl)-sodium carboxylatomethylcarbamoyl]-5-[(N-methoxyacetyl)-methylamino]-2,4,6-triiodobenzoyl derivative of 48-fold primary cascade amine;

2-{3-[(N-carboxymethyl)-methylcarbamoyl]-5-[(N-sodium carboxylatomethyl)-methylcarbamoyl]-2,4,6-triiodophenylcarbamoyl}-ethyl derivative of 48-fold primary cascade amine;

N-methoxyacetyl-3-methylamino-5-(2-sulfoethylcarbamoyl)-2,4,6-triiodobenzoyl derivative of 48-fold primary cascade amine;

3,5-di-(sodium phosphonomethylcarbamoyl)-2,4,6-triiodoarylcarbamoyl derivative of 48-fold primary cascade amine;

triacontakis-{3-(4-carboxy-3-oxabutyrylamino)-5-(2,3-dihydroxypropylcarbamoyl)-2,4,6-triiodobenzoyl}-bis-(4-carboxy-3-oxabutyryl) derivative of 48-fold primary cascade amine;

3-(4-carboxy-3-oxabutyrylamino)-5-(2,3,4,5,6-pentahydroxyhexyl-carbamoyl)-2,4,6-triiodobenzoyl derivative of 48-fold primary cascade amine; or 3-(2,3-dihydroxy-3-carboxypropionylamino)-5-(2,3-dihydroxy-propylcarbamoyl)-2,4,6-triiodobenzoyl derivative of 48-fold primary cascade amine.

\* \* \* \* \*